United States Patent
Skamser et al.

(10) Patent No.: US 10,543,061 B2
(45) Date of Patent: Jan. 28, 2020

(54) METHODS FOR MANAGING THE SCATTERING OF INCIDENT LIGHT AND ARTICLES CREATED THEREFROM

(71) Applicant: 3M INNOVATIVE PROPERTIES COMPANY, St. Paul, MN (US)

(72) Inventors: Daniel J. Skamser, Ham Lake, MN (US); Przemyslaw P. Markowicz, Woodbury, MN (US); Steven Hin-Chung Kong, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 29 days.

(21) Appl. No.: 15/513,365

(22) PCT Filed: Oct. 1, 2015

(86) PCT No.: PCT/US2015/053576
§ 371 (c)(1),
(2) Date: Mar. 22, 2017

(87) PCT Pub. No.: WO2016/054427
PCT Pub. Date: Apr. 7, 2016

(65) Prior Publication Data
US 2017/0245962 A1    Aug. 31, 2017

Related U.S. Application Data

(60) Provisional application No. 62/059,370, filed on Oct. 3, 2014.

(51) Int. Cl.
*A61C 7/20* (2006.01)
*G02B 5/02* (2006.01)
(Continued)

(52) U.S. Cl.
CPC .............. *A61C 7/20* (2013.01); *B23K 26/361* (2015.10); *G02B 5/0215* (2013.01);
(Continued)

(58) Field of Classification Search
CPC .... A61C 7/20; B23K 26/362; B23K 2101/32; G02B 5/0215; G02B 5/0221; G02B 5/0257; G02B 5/0268; G02B 5/0278; G02F 1/25
See application file for complete search history.

(56) References Cited

U.S. PATENT DOCUMENTS

| 3,504,438 A | 4/1970 | Wittman |
| 4,050,156 A | 9/1977 | Chasanoff |

(Continued)

FOREIGN PATENT DOCUMENTS

| CN | 2194079 | 4/1995 |
| CN | 1861844 | 11/2006 |

(Continued)

OTHER PUBLICATIONS

J.J. ten Bosch and J.C. Coops, ToothColor and Reflectance as Related to Light Scattering and Enamel Hardness, 1995, J Dent Res, 74, 374-380 (Year: 1995).*

(Continued)

*Primary Examiner* — Heidi M Eide
*Assistant Examiner* — Drew S Folgmann
(74) *Attorney, Agent, or Firm* — Kevin Weber

(57) ABSTRACT

The present disclosure provides engineered surfaces that exhibit reduced specular reflection and gloss while still providing a high intensity of reflected light at multiple incident angles. The structured metal surfaces include engineered topography that increases diffuse reflection, leading to a greater intensity of light perceived at multiple viewing angles. A viewer engaging such surfaces is likely to perceive (Continued)

a stronger 'white' reflection of the incident light and an improvement, particularly in orthodontic and other oral applications, of aesthetic appearance. Methods of creating the engineered surfaces and orthodontic articles incorporating the engineered surfaces are also disclosed.

13 Claims, 11 Drawing Sheets

(51) Int. Cl.
    *G02F 1/25*     (2006.01)
    *B23K 26/361*     (2014.01)
    *B23K 101/32*     (2006.01)

(52) U.S. Cl.
    CPC ......... *G02B 5/0221* (2013.01); *G02B 5/0257* (2013.01); *G02B 5/0268* (2013.01); *G02B 5/0278* (2013.01); *G02F 1/25* (2013.01); *B23K 2101/32* (2018.08)

(56) References Cited

U.S. PATENT DOCUMENTS

| | | | |
|---|---|---|---|
| 4,101,386 A | 7/1978 | Dotzer | |
| 4,107,844 A | 8/1978 | Kurz | |
| 4,219,617 A | 8/1980 | Wallshein | |
| 4,731,018 A | 3/1988 | Adell | |
| 4,948,475 A | 8/1990 | Doetzer | |
| 5,454,716 A | 10/1995 | Banerjee | |
| 5,759,029 A | 6/1998 | Kobayashi | |
| 5,813,852 A | 9/1998 | Kawaguchi | |
| 5,882,193 A | 3/1999 | Wool | |
| 6,030,209 A | 2/2000 | Panzera | |
| 6,095,809 A | 8/2000 | Kelly | |
| 6,299,438 B1 | 10/2001 | Sahagian | |
| 6,386,699 B1 | 5/2002 | Ylitalo | |
| 6,419,491 B1 * | 7/2002 | Ricci | A61C 8/0012 433/173 |
| 6,420,622 B1 | 7/2002 | Johnston | |
| 6,540,511 B1 | 4/2003 | Cavaf | |
| 6,764,709 B2 | 7/2004 | Flanagan | |
| 6,867,342 B2 | 3/2005 | Johnston | |
| 6,875,949 B2 | 4/2005 | Hall | |
| 6,984,261 B2 | 1/2006 | Cummings | |
| 7,001,672 B2 | 2/2006 | Justin | |
| 7,223,364 B1 | 5/2007 | Johnston | |
| 7,309,519 B2 | 12/2007 | Scholz | |
| 7,344,771 B2 | 3/2008 | Kubo | |
| 7,666,522 B2 | 2/2010 | Justin | |
| 7,704,073 B2 | 4/2010 | Chen | |
| 7,714,217 B2 | 5/2010 | Nesbitt | |
| 7,811,623 B2 | 10/2010 | Nesbitt | |
| 8,088,325 B2 | 1/2012 | Toyota | |
| 8,632,848 B2 | 1/2014 | Shin | |
| 8,726,510 B2 | 5/2014 | Voudouris | |
| 8,778,444 B2 | 7/2014 | Kim | |
| 8,999,445 B2 | 4/2015 | Henze | |
| 9,370,404 B2 | 6/2016 | Velamakanni | |
| 9,388,070 B2 | 7/2016 | Henze | |
| 9,539,182 B2 | 1/2017 | Morris | |
| 2002/0128578 A1 | 9/2002 | Johnston | |
| 2003/0011730 A1 | 1/2003 | Yoshii | |
| 2003/0210368 A1 | 11/2003 | Yoshii | |
| 2003/0235677 A1 | 12/2003 | Hanschen | |
| 2004/0219323 A1 | 11/2004 | Kubo | |
| 2005/0123672 A1 | 6/2005 | Justin | |
| 2005/0214709 A1 | 9/2005 | Chen | |
| 2006/0166159 A1 * | 7/2006 | Abels | A61C 7/14 433/8 |
| 2006/0199139 A1 | 9/2006 | Chen | |
| 2006/0204919 A1 | 9/2006 | Thiry | |
| 2007/0134610 A1 | 6/2007 | Wyllie, II | |
| 2007/0134784 A1 | 6/2007 | Halverson | |
| 2007/0172788 A1 | 7/2007 | Hill, II | |
| 2008/0274440 A1 * | 11/2008 | Smith | A61C 8/005 433/174 |
| 2009/0186313 A1 | 7/2009 | Chen | |
| 2010/0119755 A1 | 5/2010 | Chung | |
| 2010/0255447 A1 | 10/2010 | Biris | |
| 2010/0290250 A1 | 11/2010 | Toyota | |
| 2010/0330522 A1 | 12/2010 | Hirsch | |
| 2011/0220612 A1 | 9/2011 | Kim | |
| 2012/0064240 A1 | 3/2012 | Liu | |
| 2012/0128864 A1 | 5/2012 | Shin | |
| 2012/0135367 A1 | 5/2012 | Foerster | |
| 2012/0295081 A1 | 11/2012 | Henze | |
| 2013/0130201 A1 | 5/2013 | Smith | |
| 2013/0157225 A1 | 6/2013 | Morris | |
| 2013/0171589 A1 | 7/2013 | Velamakanni | |
| 2013/0180627 A1 | 7/2013 | Miura | |
| 2014/0106905 A1 | 4/2014 | Morgan | |
| 2014/0227653 A1 | 8/2014 | Kalkhoran | |

FOREIGN PATENT DOCUMENTS

| | | |
|---|---|---|
| CN | 101219008 | 7/2008 |
| CN | 101219590 | 7/2008 |
| CN | 101245459 | 8/2008 |
| CN | 201164095 | 12/2008 |
| CN | 201622769 | 11/2010 |
| CN | 201855312 | 6/2011 |
| CN | 202015260 | 10/2011 |
| DE | 29924586 | 12/2003 |
| DE | 10252529 | 8/2004 |
| DE | 1796573 | 6/2007 |
| DE | 2045350 | 4/2009 |
| DE | 202009008570 | 8/2009 |
| EP | 2359772 | 8/2011 |
| FR | 2681181 | 3/1993 |
| JP | 0438948 | 2/1992 |
| JP | 04237532 | 8/1992 |
| JP | 0612927 | 1/1994 |
| JP | 08140995 | 6/1996 |
| JP | 08199395 | 8/1996 |
| JP | 2004236772 | 8/2004 |
| JP | 2005323694 | 11/2005 |
| JP | 2006192199 | 7/2006 |
| JP | 2008086633 | 10/2006 |
| JP | 2009017996 | 1/2009 |
| JP | 2009523542 | 6/2009 |
| JP | 4475458 | 6/2010 |
| JP | 2012509131 | 4/2012 |
| KR | 20070064987 | 6/2007 |
| KR | 20090015009 | 2/2009 |
| KR | 101033025 | 5/2011 |
| KR | 20110121431 | 11/2011 |
| KR | 101136551 | 4/2012 |
| KR | 20120082556 | 7/2012 |
| KR | 101297644 | 8/2013 |
| PL | 382449 | 11/2008 |
| TW | 200932197 | 8/2009 |
| WO | WO 1997-29712 | 8/1997 |
| WO | WO 1999-52667 | 10/1999 |
| WO | WO 2000-13605 | 3/2000 |
| WO | WO 2004-000569 | 12/2000 |
| WO | WO 2007-084387 | 7/2006 |
| WO | WO 2007-070310 | 6/2007 |
| WO | WO 2009-045036 | 4/2009 |
| WO | WO 2009-094684 | 8/2009 |
| WO | WO 2010-058925 | 5/2010 |
| WO | WO 2010-141261 | 12/2010 |
| WO | WO 2012-021438 | 2/2012 |
| WO | WO 2012-030565 | 3/2012 |
| WO | WO 2013-122365 | 8/2013 |
| WO | WO 2014-093119 | 6/2014 |
| WO | WO 2015-088976 | 6/2015 |

OTHER PUBLICATIONS

Ahsan, Shamim, Md., et al., "Colorizing Stainless Steel Surface by Femtosecond Laser Induced Micro/Nano-Structures," Applied Sur-

(56) References Cited

OTHER PUBLICATIONS face Science, © 2011 Elsevier B.V. All Rights Reserved, pp. 7771-7777.

Mahmood et al., "3-D Aluminum Nanostructure with Microhole Array Synthesized by Femtosecond Laser Radiation for Enhanced Light Extinction," Nanoscale Research Letters, 2013; http://www.nanoscalereslett.com/content/&/1/477, © 2013.

Gomez-Polo, et al., Study of the Shade Tabs of the Toothguide 3D Master Through Cluster Analysis, © 2014 Wiley Periodicals, Inc., pp. 194-200.

Abramowitz, "Specular and Diffuse Reflection", [retrieved from the internet on May 22, 2017], URL <http://micro.magnet.fsu.edu/primer/java/reflection/specular/>, 1998, .pp. 1-2.

Aksoy, "New Measures of Whiteness that Correlate with Perceived Color Appearance", Department of Chemical Engineering, 2012, pp. 1-41.

Dentsply Gac, "High Aesthetic Archwires: Sentalloy® and BioForce®", 2007, pp. 1-2.

Dentsply Gac, "High Esthetic Archwires: Sentalloy®, BioForce® and Stainless Steel", [retrieved from the internet on May 22, 2017], URL <http://www.tocdental.com/userfiles/file/120-002-01.pdf>, 2010, pp. 1-2.

Laakso, "Relation of Laser Parameters in Color Marking of Stainless Steel", Fraunhofer Center for Laser Technology, [retrieved from the internet on May 22, 2017], URL <http://www.vtt.fi/files/research/ism/manufacturingsystems/relation_of_laser_parameters_in_color_marking_of_stainless_steel.pdf>, pp. 1-15.

Lemkuhl, "The Principles and Techniques of Electrolytic Aluminum Deposition and Dissolution in Organoaluminum Electrolytes", Advances in Electrochemical Science and Engineering, 1994, vol. 177, pp. 163-226.

International Search Report for PCT International Application No. PCT/US2015/53576, dated Dec. 28, 2015, 3 pages.

\* cited by examiner

METHODS FOR MANAGING THE SCATTERING OF INCIDENT LIGHT AND ARTICLES CREATED THEREFROM

BACKGROUND

Orthodontic therapy is a specialized area of dentistry concerning the supervised treatment of malpositioned (or crooked) teeth. Generally such treatment involves the judicious application of light continuous forces to the teeth using one or more orthodontic appliances. These forces stimulate changes in surrounding bone structure, thereby gradually directing teeth to their proper locations in the oral cavity. Orthodontic therapy can provide many benefits, including ease of maintaining hygiene, improved facial appearance, as well as improved bite function.

Fixed appliances, or "braces," represent one type of orthodontic treatment in which tiny slotted appliances, called brackets, are attached to the teeth. A resilient, U-shaped (i.e., parabolic) archwire is then placed into the slots of the brackets. When ligated to the brackets, the archwire acts as a track that guides teeth toward their proper locations during the course of treatment. In the beginning of treatment, the archwire tends to have small cross-sectional dimensions to facilitate ligation and also keep forces imparted to the teeth relatively low as the teeth unravel. In later stages of treatment, the teeth approach their target positions, allowing for progressively larger (and stiffer) wires to be used to improve the practitioner's control over the associated teeth.

Orthodontic brackets may be made from a range of different materials such as metals (e.g., stainless steel), plastics (e.g., polycarbonate) and ceramic materials such as monocrystalline and polycrystalline aluminum oxide. Archwires may also be made from a range of metal or metal alloy materials including stainless steel, titanium, and shape memory alloys such as alloys of nickel-titanium and copper-nickel-titanium.

SUMMARY

Many orthodontic appliances, and in particular metallic archwires, remain aesthetically unappealing to certain patients and practitioners due, at least in part, to metallic luster and recognizable contrast with the color (white or otherwise) of the patient's enamel. In recent decades, interest has increased in the use of aesthetic orthodontic brackets that tend to minimize the appearance of metal in the oral cavity. For example, ceramic orthodontic brackets have now been developed that are translucent and assume the color of the underlying tooth. Translucent plastic brackets and tooth-colored plastic brackets are also known.

The use of aesthetic orthodontic brackets can present a significantly improved appearance in the oral cavity. Oftentimes, the arch wire is the only metal component that is readily visible. Consequently, it would be desirable to reduce or eliminate this last remaining source of metallic appearance.

Orthodontic archwires that are coated with a non-metallic aesthetic layer have been proposed in the past. For example, U.S. Pat. No. 5,454,716 (Banerjee et al.) and International Publication No. WO 97/29712 (Sjoegren) describe orthodontic archwires that are coated with a thin coloring layer that matches the color of the teeth. Other coated orthodontic archwires are described in U.S. Pat. No. 4,050,156 (Chasanoff et al.) and U.S. Pat. No. 3,504,438 (Anthony et al.). U.S. Pat. No. 4,731,018 (Addle et al.) describes an archwire with a metal part and a plastic part arranged so that the plastic part faces in a labial direction.

Previous attempts to improve the appearance of metal orthodontic article have also featured deposition or introduction of aesthetic metals onto one or more surfaces of the article. U.S. Pat. No. 8,778,444 (Kim) describes the physically or chemically etching of a surface of the metal wire prior to coating the surface with a metal or other protective composition to impart a white or ivory color. The archwire is subsequently coated with a transparent parylene film, ostensibly so that the transparent metal material can be prevented from discoloration and coherence between the wire and the teeth. Similarly, U.S. Pat. No. 8,726,510 (Voudouris) reports the use of large scale, laser created craters on a self-ligating bracket clip to generate a roughened surface texture for enhanced aesthetic coating adhesion.

U.S. Pat. No. 5,882,193 (Wool) sets forth a means for attaching auxiliary parts to an archwire, whereby a surface of an archwire is first de-oxidized by treatment with acid reducing agents. The cleaned surface is then plated with a noble metal e.g., gold, platinum, rhodium and palladium. The plated surface can provide some aesthetic improvement, while primarily providing a solderable or brazable surface for auxiliary attachment.

By relying primarily on the affects imparted by the coating materials, such methods produce orthodontic appliances that are still unmistakably metallic in appearance, particular as the relative orientation of the dental arch changes during speech, mastication, and other movements of the head. What is needed, accordingly, is an appliance that substantially maintains a tooth colored appearance at a wide range of viewing angles while minimizing metallic luster.

The present disclosure provides engineered, structured metal surfaces that exhibit reduced specular reflection and gloss while still providing a high intensity of reflected light at multiple incident angles. The structured metal surfaces include engineered topography that increases diffuse reflection, leading to a greater intensity of light perceived at multiple viewing angles. A viewer engaging such surfaces is likely to perceive a stronger 'white' reflection of the incident light and an improvement, particularly in orthodontic and other oral applications, of aesthetic appearance.

In one aspect, the present disclosure provides an orthodontic appliance including an exterior surface including metal; and a plurality of recesses in the exterior surface, and wherein the surface including the plurality of recesses exhibits a Total CIE Chroma of no greater than 14 and a minimum $L^*$ value of at least 20 at an incident angle of 0 degrees and a view angle of 70 degrees.

In another aspect, the present disclosure provides an orthodontic appliance including an exterior surface including metal; and a plurality of engineered features in the exterior surface, and wherein the surface including the plurality of engineered features exhibits a Total CIE Chroma of no greater than 14 and a minimum $L^*$ value of at least 20 at an incident angle of 0 degrees and a view angle of 70 degrees.

In another aspect, the present disclosure provides an appliance including a body having an exterior surface including metal and a plurality of engineered features on the surface. The engineered surface exhibits a diffuse $L^*$ min70/max15 ratio of at least 0.2 at a Total CIE Chroma of less than 14, a minimum $L^*$ value of at least 20 at an incident angle of 0 degrees and a view angle of 70 degrees, as measured by the Diffuse Scattering Test.

In another aspect, the present disclosure provides an appliance including an exterior surface including a metal and a plurality of recesses defined in the surface. The recesses have an average depth from the surface of at least 0.5 microns and are arranged in overlapping arrays such that a majority of the recesses overlap with adjacent recesses at boundary regions.

In yet another aspect, the present disclosure provides a method for improving the aesthetic appearance of an article, the method including providing an article having an exterior surface, the surface including metal, and ablating at least a portion of the surface to create a plurality of features thereon, such that the surface exhibits a diffuse L* min70/max15 ratio of at least 0.2.

As used herein "geometry" refers to the size and shape of an engineered feature.

As used herein, a "feature" is a structure or feature having a recognizable geometric shape defined by a volume that projects out the base plane of a surface or an indented volume which projects into the surface.

As used herein, an "engineered microstructure" and "engineered feature" shall mean a structure deliberately formed into and integral with a surface. An engineered microstructure or engineered feature are distinct from structures produced by random application of particles, by spraying, adhesive bonding, etc., to a surface.

As used herein, the terms "engineered surface" and "structured surface" are generally used to refer to a surface that comprises engineered features.

As used herein, the term "pitch" means the average centroid to centroid distance between adjacent structures (e.g., recesses) on the engineered surface.

As used herein, the terms "height", "base" and "top" are for illustrative purposes only, and do not necessarily define the orientation or the relationship between the surface and the microstructure. For example, the "height" of a feature projected into a surface can be considered the same as the "depth" of recess created, and the "top" the "bottom" of said recess. Accordingly, the terms "height" and "depth", as well as "top" and "bottom" should be considered interchangeable.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As recited herein, all numbers should be considered modified by the term "about".

As used herein, "a," "an," "the," "at least one," and "one or more" are used interchangeably. Thus, for example, an engineered surface comprising "a" pattern of recesses can be interpreted as an engineered surface comprising "one or more" patterns.

Also herein, the recitations of numerical ranges by endpoints include all numbers subsumed within that range (e.g., 1 to 5 includes 1, 1.5, 2, 2.75, 3, 3.80, 4, 5, etc.).

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

The above summary of the present disclosure is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exhaustive list.

BRIEF DESCRIPTION OF THE DRAWINGS

The disclosure will be further described with reference to the drawings, wherein corresponding reference characters indicate corresponding parts throughout the several views, and wherein.

Figure 1:
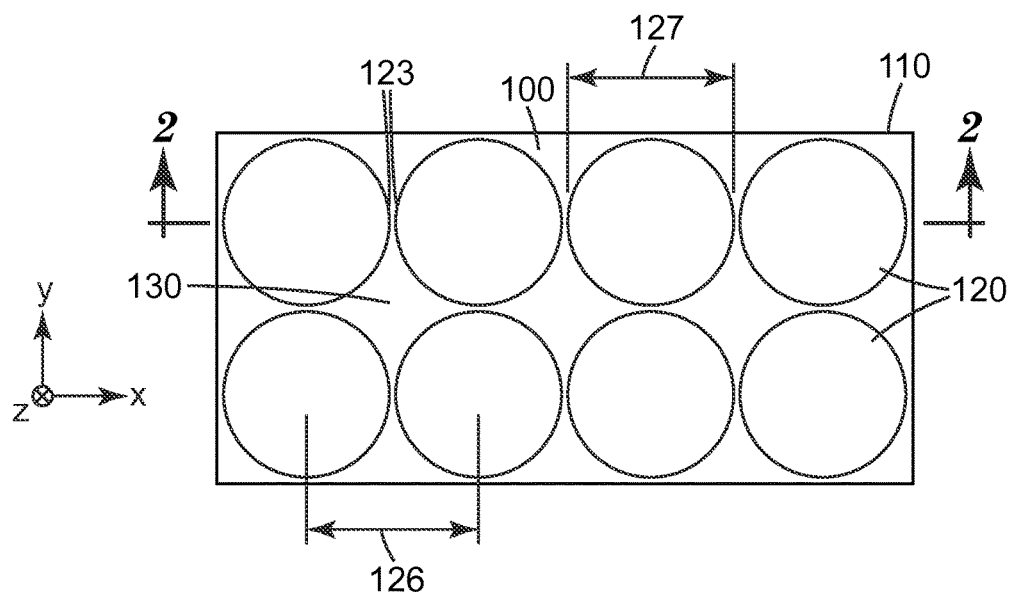
FIG. 1 illustrates an arrangement of engineered recesses on a surface, according to one embodiment of the present disclosure.

Layers in certain depicted embodiments are for illustrative purposes only and are not intended to absolutely define the thickness, relative or otherwise, or the absolute location of any component. While the above-identified figures set forth several embodiments of the disclosure other embodiments are also contemplated, as noted in the description. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF ILLUSTRATIVE EMBODIMENTS

Engineered Surfaces

The present disclosure provides engineered, structured metal surfaces that exhibit reduced specular reflection and gloss while still providing a high intensity of reflected light at a wide range of incident angles. The structured metal surfaces include engineered topography that increases diffuse reflection, leading to a greater intensity of light perceived at a wide range of viewing angles. A viewer engaging such surfaces is likely to perceive a strong 'white' reflection of the incident light and an improvement, particularly in orthodontic and other oral applications, of aesthetic appearance. Advantageously, the creation of structures according to the methods and concepts below eliminates or substantially reduces any deleterious effect on the mechanical performance of the substrate or an article containing the substrate.

A structured surface region extends generally along orthogonal in-plane directions, which can be used to define a local Cartesian x-y-z coordinate system. The topography of the structured surface region can then be expressed in terms of deviations along a thickness direction (z-axis), relative to a reference plane (the x-y plane) lying parallel to the structured surface. The engineered or structured surface region of the substrate can also be generally described in terms of an average elevation. The average elevation of the structured surface region can be defined as an imaginary surface associated therewith i) lacking protrusive features or intrusive features and ii) being parallel to a major surface contour of the substrate in the structured surface region. The major surface contour of the substrate can be referred to as the shape of the surface of the substrate surface, regardless of the shape of the protrusive features and the intrusive features of the structured surface region. The structures are typically limited in size along two orthogonal in-plane directions, i.e., when the structured surface is seen in plan view, individual structures do not typically extend indefinitely in a linear fashion along any in-plane direction. Engineered surface regions of the present disclosure comprise intrusive features and, in certain embodiments, protrusive features. Protrusive features of an engineered surface region can generally be described as features having surface points that lie above the average elevation of the structured surface region. Intrusive features (e.g., recessed features) of the structured surface region can generally be described as features having surface points that lie below the average elevation of the structured surface region. In some contexts herein, protrusive features and intrusive features are features commonly referred to as topographical features.

Engineered surfaces or surface regions having intrusive features can be referred to as recessed features or recesses. Recessed features, for example, can be referred to as recesses, wells, cavities, concavities, pockets, channels, and the like. Recessed features can have a volume with dimensions such as diameter, radius, depth, length, and width. A base of the recessed feature can generally refer to a location within the recessed feature having points lying closest to an average elevation, while the surface or region of the recess farthest from the average elevation is considered an apex. In some embodiments, a recessed feature can be separated from another recessed feature by adjacent protrusive features.

The base of each topographical feature may comprise a variety of cross-sectional shapes including, but not limited to, parallelograms, parallelograms with rounded corners, rectangles, squares, circles, half-circles, ellipses, half-ellipses, triangles, trapezoids, stars, other polygons (e.g., hexagons), etc., and combinations thereof. For irregularly shaped bases (e.g., bases which are not parallelograms or circles) the relevant cross-sectional dimension will be understood to be the diameter of a circle of equivalent area.

Protrusive features of the structured surface regions can be features that represent a departure or deviation away from an otherwise flat surface region. In some presently desirable embodiments, protrusive features separate recessed features. In some embodiments, the geometry of the structured surface region can be described as hierarchical. For example, within the structured surface region, recessed features can have random, partially random, or precisely spaced features positioned on the surfaces or walls of the recessed features, on raised regions of the recessed features, and within the recessed features. The surfaces of the recessed features can include protrusive features on a shorter height or narrower width scale than that characteristic of the recessed feature itself, for example.

In some embodiments, the topographical features are distributed as a periodic array across a structured surface region (e.g., a one-dimensional array or a two-dimensional array, for example a square array, hexagonal, or other regular array). In some embodiments, the structured surface includes an arranged pattern of recesses. An "arranged pattern of recesses" is a plurality of recesses arranged at predetermined positions, arranged with some degree of regularity, or arranged in any desired manner. For example, the arranged pattern of recesses can include an arranged row pattern, an arranged lattice pattern such as an arranged square lattice pattern, an arranged zigzag pattern, or an arranged radial pattern. The arranged pattern of recesses need not be formed evenly on the entire surface but may be formed in only a portion of the article surface. The pattern of recesses may vary or remain the same over any portion of the article. For example, similar or different patterns can be used within the same plane. The recesses within the pattern can be of similar size and shape or can have different sizes and shapes.

In some embodiments, features of the structured surface region can be present on a regular repeating basis, on a random basis, and the like, or combinations thereof. In other embodiments, the features can be present over a portion of the entire area of the structured surface region, or present over the entire area of the structured surface region. In some embodiments, features can be present in the recessed features of the structured surface region, present on the protrusive features of the structured surface region, and the like, or combinations thereof.

Whether protrusions or recesses, the structures may also in some cases be closely packed, i.e., arranged such that at least portions of boundaries of many or most adjacent structures substantially meet, coincide, of substantially overlap. The structures can be irregularly or non-uniformly dispersed on the structured surface. In some cases, some, most, or substantially all (e.g., >90%, or >95%, or >99%) of the structures may be curved or comprise a rounded or otherwise curved base surface. The size of a given structure may be expressed in terms of an equivalent circular diameter (ECD) in plan view, and the structures of a structured surface may have an average ECD of less than 70 microns, or less than 60 microns, or in a range from 5 to 50 microns, for example. The structured surface region and structures can also be characterized with other parameters as discussed elsewhere herein, e.g., by an aspect ratio of the depth or height to a characteristic transverse dimension such as ECD.

Figure 2:
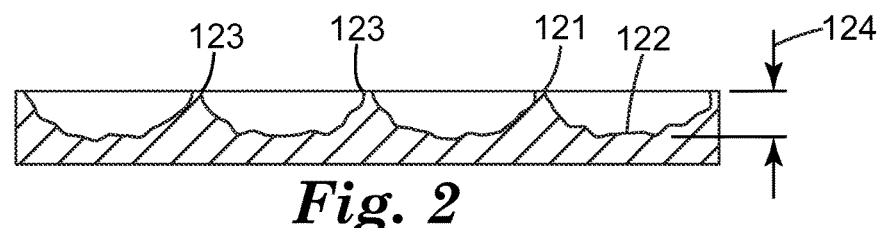
FIG. 2 is a cross-sectional view of the engineered surface of FIG. 1.

An engineered surface 110 according to one implementation of the present disclosure is illustrated in FIGS. 1-2 and includes a plurality of discreet engineered recesses 120 projecting into at least a portion of a metal substrate 100. The metal substrate 100 may be planar, substantially planar, or include varying topography (e.g., undulations). Suitable metals for use as the substrate include, but are not limited to, stainless steel alloys, chromium-cobalt-molybdenum alloys, titanium alloys, zirconium alloys, shape memory nickel-titanium alloys, super elastic nickel-titanium alloys, aluminum alloys, copper alloys, and combinations thereof. Additional metals may be used depending on the desired application for the engineered surface. The thickness of the substrate 100 can vary depending on the intended use of the engineered surface. Advantageously, the engineered features are typically made from the same materials as the substrate, as further described below.

The engineered recesses 120 are arranged in an array having a defined spacing or pitch between adjacent recesses 120. The configuration of recesses in any given region is chosen so that the pitch 126 (i.e., the average centroid to centroid distance between adjacent features) is at least 5 microns, in other embodiments at least 15 microns, in other embodiments at least 20 microns, in other embodiments at least 25 microns, and in yet other embodiments at least 30 microns. In certain embodiments, the pitch 126 is no greater than 70 microns, in some embodiments no greater than 60 microns, in some embodiments no greater than 50 microns, and in certain embodiments no greater than 45 microns. Engineered surfaces having feature pitches outside this range, depending on the cross-sectional dimensions of the recesses, may result in topographies that do not sufficiently reduce specular reflection or do not provide sufficient topographical hierarchy, leading to a glossy or metallic appearance. Without wishing to be bound by theory, when the pitch is too large, the perceived brightness and gloss will be more dependent on the non-patterned surfaces than the engineered structures, particularly when the feature geometry (e.g., diameter, height) is small. If recesses are created via introduction of laser energy according to methods described below, a pitch below 5 microns can result in excess thermal energy introduced over a given surface area at high repetition rates. This excess introduction of thermally energy may, in certain circumstances oxidize the metal and/or may distort the grain structure, potentially altering mechanical properties of the engineered surface and the attendant article.

A Cartesian x-y-z coordinate system is included in FIG. 1 for reference purposes. The substrate extends generally parallel to the x-y plane, and an optical axis of the system may correspond to the z-axis. The lattice array of engineered recesses 120 includes a transverse direction, generally along the x-axis and a longitudinal direction, generally along the y-axis. The pitch between adjacent recesses in an array or pattern may be the same in both the traverse direction and longitudinal direction. In other potentially advantageous embodiments, the pitch along the longitudinal direction is less than the pitch along the transverse direction and vice versa. The ratio between the pitch along the transverse direction and the pitch along the longitudinal direction is defined herein as the spacing ratio. In certain circumstances, particularly when multiple patterns are overlaid according to methods described below, it may be preferred that the spacing ratio is not 1:1, as a spacing ratio of 1:1 may produce a visible Moire pattern perceptible on the surface and potentially distracting from the desired aesthetic appearance.

In some embodiments, the spacing ratio is 0.7:1, in some embodiment 0.9:1, in some embodiments 1.1:1, in some embodiments 1.3:1, and in yet other embodiments 1.5:1.

As seen in FIG. 1, the engineered recesses 120 in the depicted embodiment are arranged in a cubic array, in that the boundary regions 123 of adjacent recesses 120 are directly adjacent or slightly overlapping (i.e., a discreet diameter of the recesses may be calculated in non-overlapping regions). The engineered recesses 120 are essentially discreet and include interstitial space 130 between adjacent recesses 120. The interstitial space 130 is, in this implementation, un-patterned in that it generally lacks any topographical or hierarchical features. Without wishing to be bound by theory, un-patterned bare metal substrate between adjacent recesses may, in some circumstances, deleteriously affect the appearance of the substrate or article, as the un-patterned regions allow for more specular reflection of incident light (i.e., gloss).

In a closely packed array, however, the effect of the un-patterned surface regions may be reduced or even minimized. As shown in optical micrograph image of FIG. 4, an engineered surface may include an arrangement of recesses in a hexagonal close packed array to further minimize the interstitial space between adjacent recesses.

Due to the tendency of a flat metal surface to cause specular reflection of incident light and increase gloss, the area of the engineered surface contained within the plurality of recesses is typically substantially greater than the area bound within interstitial spaces. In some embodiments, 75% of the area of the engineered surface is contained within the recesses, in some embodiments at least 80%, in some embodiments at least 85%, in some embodiments at least 90%, and in yet additional embodiments at least 95% of the area is contained within the recesses.

Generally, recesses 120 comprise a base 121 adjacent the engineered surface 110 and a bottom surface or apex 122 separated from base 121 by a depth 124. A recess 120 typically includes a spherical surface or concavity such that the depth near the perimeter or boundary is less than that near the center. As used herein, the term "spherical surface" means that the surface can be considered to be a portion of a sphere or the surface has a generally spherical curvature. Some spherical surfaces can be considered to be dome-shaped or hemispherical. Other spherical surfaces can cover a smaller portion of a sphere than a hemisphere. In certain implementations, the spherical curvature of the recess 120 is generally continuous, such that the recess lacks sidewalls that are orthogonal or substantially orthogonal (e.g., 80—89 degrees) to the engineered surface. The general spherical curvature in such implementations can be considered independent of hierarchical protrusive features within the recess.

The base 121 of each engineered recess 120 may comprise a variety of cross-sectional shapes including, but not limited to, parallelograms, parallelograms with rounded corners, rectangles, squares, circles, half-circles, ellipses, half-ellipses, triangles, trapezoids, stars, other polygons (e.g., hexagons), etc., and combinations thereof. Regardless of cross-sectional shape, each engineered feature comprises a largest cross-sectional dimension at the base 121. In presently preferred implementations, the largest cross-sectional dimension of the base 121 may be no greater than 80 microns, in some embodiments no greater than 70 microns, and in some embodiments no greater than 60 microns. The largest cross-sectional dimension may be at least 10 microns, in some embodiments at least 15 microns, and in some embodiments at least 20 microns. As will be set forth in the Examples below, recesses having a largest cross-sectional dimension outside this range can be either perceivable by the naked eye and/or can result in insufficient modification of the substrate surface.

A recess 120 typically includes a depth no greater than the pitch or largest cross-sectional dimension 127, though in certain embodiments the recess depth is significantly less than the pitch or cross-sectional dimension. Generally, each recess of the plurality of recesses has a depth that is at least 0.5 microns. In some embodiments, recesses have a depth of at least 1 micron, in other embodiments at least 1.5 microns, in other embodiments at least 2 microns, in other embodiments at least 3 microns and in other embodiments at least 5 microns. In certain embodiments, the recess depth is no greater than 30 microns, in some embodiments no greater than 25 microns, in some embodiments no greater than 20 microns, and in certain embodiments no greater than 15 microns. Recesses having a depth greater than 30 microns may trap certain wavelengths of light, leading to less available intensity for the surface to appear sufficiently white. It may be noted, however, that not all recesses of the plurality of recesses need fall within the depth range listed above.

Each recess 120 of the plurality of recesses includes a particular aspect ratio. For recesses comprising regular (e.g., Euclidean) and irregular (e.g., Non-Euclidean) cross-sectional shapes substantially throughout the height of the microstructure, the aspect ratio is defined herein as the ratio of the depth to the largest cross-sectional dimension (e.g., width, length, diameter) at the base. For irregularly shaped bases (bases which are not parallelograms or circles) the largest cross-sectional dimension will be understood to be the diameter of a circle of equivalent area. Regardless of recess geometry, each recess of the plurality of recesses typically includes an aspect ratio of no greater than 0.75 and at least 0.08.

As briefly mentioned above, certain recesses of the plurality of recesses 120 can include hierarchical protrusive features thereon or therein. The protrusive features are typically submicron scale or at least include height and cross-sectional dimensions appreciably smaller than the cross-sectional dimension 127 or depth 124 of the recess 120. In certain embodiments, these hierarchal features may be created as a result of the methods used to create the recess 120, particularly those methods featuring laser ablation as further described below. In other implementations, the protrusive features may be added subsequent to the creation of the recesses by known methods for disposing microscale and nanoscale structures on a surface. The protrusive features may enhance the diffuse reflection of light and may interfere with an otherwise perceivable pattern of features that can otherwise detract from the aesthetic appearance of the engineered surface 110.

Figure 3:
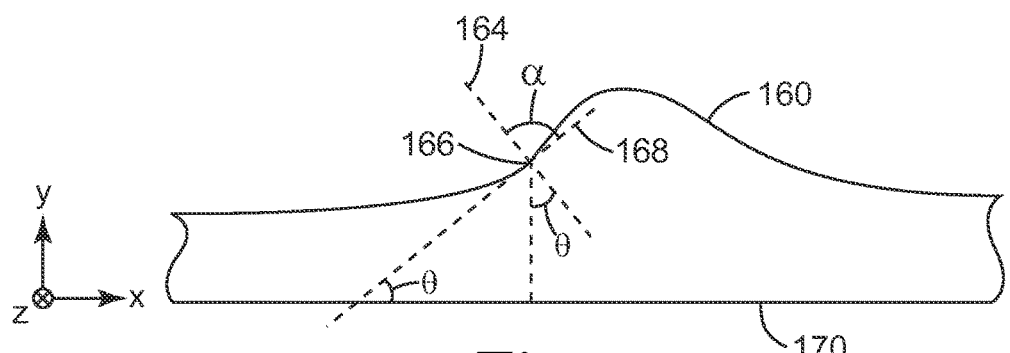
FIG. 3 is a schematic side-view of an engineered structure.

The engineered surfaces of the present disclosure can be characterized, for example, by the slope distribution and surface roughness of the attendant engineered features. Representative portions of the engineered surfaces can be and were characterized using confocal scanning laser microscopy (50×-150× objective). FIG. 3 is a schematic side-view of a portion of an article including an engineered surface. In particular, FIG. 3 shows an engineered feature 160 that has a slope distribution across the surface of the feature. For example, the microstructure has a slope θ at a location 166 where θ is the angle between normal line 164 which is perpendicular to the engineered feature surface at location 166 (α=90 degrees) and a tangent line 168 which is tangent to the feature surface at the same location. Slope θ is also the angle between tangent line 168 and a planar, major surface of the article 170.

Slope of the structured surface can be taken along an x direction, and then along a y direction, such that:

$$X - \text{slope} = \frac{\Delta H(x, y)}{\Delta x}, \text{ and} \qquad \text{Equation 1}$$

$$Y - \text{slope} = \frac{\Delta H(x, y)}{\Delta y} \qquad \text{Equation 2}$$

Where, H(x,y)=the height profile of the surface.

Average x-slope and y-slope were evaluated in a 1.65 micron interval about each pixel. In different embodiments the interval may be chosen to be larger, such as 2 microns, or 3 microns, so long as a constant interval is used. X and y slope distributions were generated with a bin size of 0.5 degrees. From the x-slope and y-slope data, it is possible to determine a gradient magnitude. This may be understood as follows:

$$\text{Gradient Magnitude} = \sqrt{\left(\frac{\Delta H(x, y)}{\Delta x}\right)^2 + \left(\frac{\Delta H(x, y)}{\Delta y}\right)^2} \qquad \text{Equation 3}$$

Average gradient magnitude was then capable of being evaluated in a 1.65 μm×1.65 μm box centered at each pixel. Gradient magnitude distribution was generated with a bin size of 0.5 degrees. It should be understood that in order to find the angle degree value of the x-slope, y-slope and gradient magnitude angles that corresponds to the values above, the arctangent of the values in Equations 1, 2, and 3 should be taken. Gradient magnitude corresponds to a combination of the x and y-slopes, and therefore, gradient magnitude may be understood as a general slope magnitude.

In some cases, such as when the engineered features have a Gaussian or normal slope distribution, the minimum full width at half maximum (FWHM) between the x-slope distribution and the y-slope distribution is at least 10 degrees, in other embodiments at least 20 degrees, and in yet other embodiments at least 30 degrees. A minimum FWHM of at least 20 degrees evinces a variety of features that tend to increase the intensity of diffuse, reflected light. Other exemplary slope distributions include Lorentzian distributions, parabolic distributions, and combinations of different, distributions.

In addition to the minimum FWHM of the slope distribution and the slope magnitude, the surface roughness of the engineered surface can also impact the light reflective properties. As should be self-evident, surface roughness is a measure of the roughness of a surface. Surface roughness can be measured using a technique such as confocal microscopy that can resolve features in the micrometer range. When describing surface roughness, either average roughness (Ra) or root-mean-square roughness (Rq) can be used, though Rq is presently preferred. Rq is the root mean square average of height deviations taken from the mean image data plane, expressed as:

$$Rq = \sqrt{\frac{\Sigma H_i^2}{N}} \qquad \text{Equation 4}$$

where N is the total number of points and H is the height at each point (relative to the mean height).

Fourier analysis of the raw data can be used to examine roughness of the engineered surface while minimizing contributions from noise and surface waviness. A high spatial frequency filter can be used to remove waviness. Alternatively, a low pass spatial frequency filter can be used to remove noise introduced by the measuring instrument. When using a low pass spatial frequency filter, a high pass spatial frequency filter may be used in conjunction with the low pass filter to remove waviness and noise in the surface height map of the sample (i.e., a band pass filter). A Gaussian Fourier filter window is typically used to avoid ringing artifacts as is known in the art. See for example, ASME standard B46.1-2009: "Surface Texture: Surface Roughness, Waviness, and Lay" and ISO 25178-2:2012. It is understood by those of ordinary skill in the art, that the roughness measurements should typically be taken in a region of the sample without debris or defects (e.g., unintentional bubbles, pits, scratches, etc.) to be meaningful. Software programs such as those available under the trade designation "VISION" from Bruker Corp., Santa Barbara, Calif. may be used or data processing software such as those programs available under the trade designation "MATLAB" from MathWorks, Natick, Mass. may be used. In one embodiment, using a Gaussian Fourier filter, the Rq value for the engineered surface is greater than 0.5, 0.8, 1, 1.5 or even 2 microns. In presently preferred circumstances, the Rq value of the engineered surface is at least 1 micron.

Figure 4:
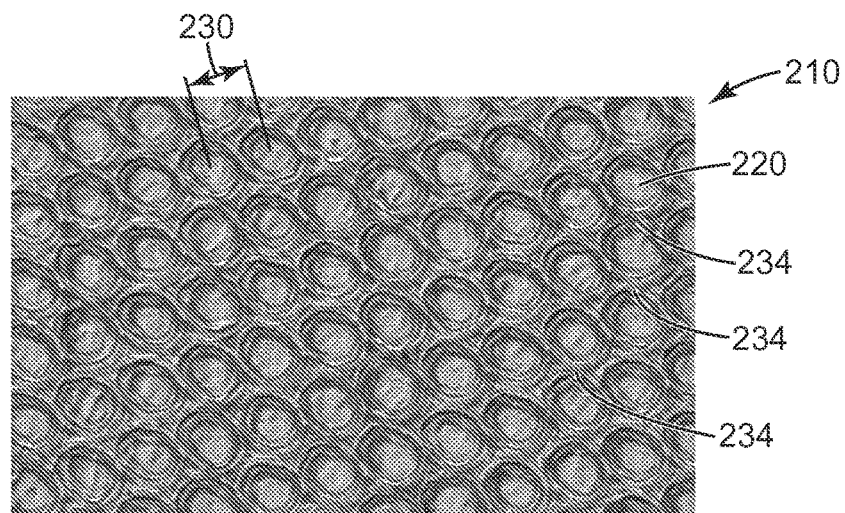
FIG. 4 is an optical micrograph of a pattern of engineered recesses according to another embodiment of the present disclosure.

An engineered surface 210 according to another embodiment of the present disclosure is shown in the optical micrograph of FIG. 4. The engineered surface 210 includes an arrangement of disrupted recesses 220 having a modified cross-sectional dimension at the recess base 234. Disrupted recesses 220 according to the present disclosure can be the result of overlap of boundary regions between adjacent recesses. To create such overlap, disrupted recesses 220 are created based on an expected diameter that is greater than the pitch 230. An "expected diameter" as used herein means the diameter or ECD at the base of a single recess according to the selected method and process parameters used in creating the engineered surface. For example, a recess 220 created via laser ablation according to the methods described below may have an expected diameter of 40 microns. If multiple recesses 220 are arranged along a transverse direction of the metal surface at a pitch of 30 microns, there will be roughly 10 microns of overlap between adjacent recesses 220. Additional overlapping regions may be created by adjacent recesses in the longitudinal direction as well. The overlapping region may result in protrusive or intrusive features created between discreet recesses, and alternatively may appear to the naked eye as part of a recess or as interstitial space.

Figure 5:
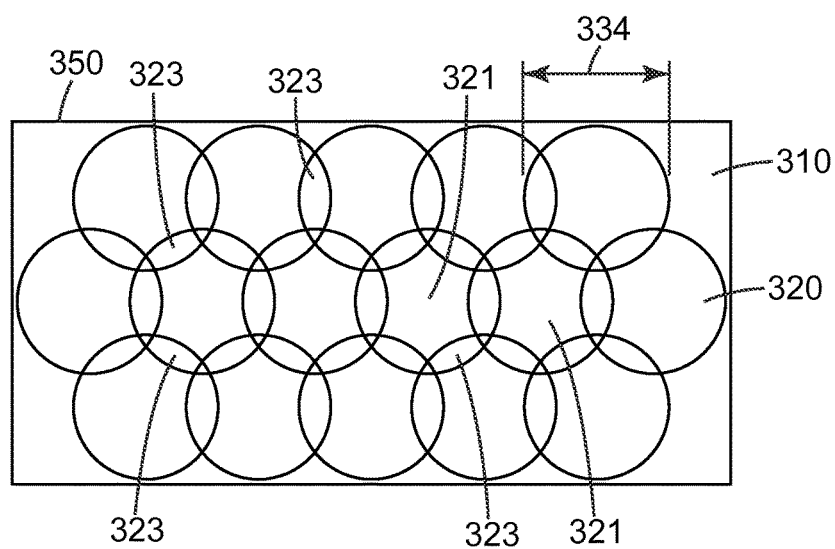
FIG. 5 is an illustration of an arrangement of overlapping, engineered recesses according to another embodiment of the present disclosure.

The concept of disrupted recesses is further illustrated in FIG. 5. FIG. 5 depicts a plurality of spherical recesses 320 having an expected diameter 334. The recess are arranged in a linear, grid array, such that any recess 320 not disposed on an edge region 350 of the engineered surface 310 will have one or more adjacent recesses 320 in the x and y directions. Certain recesses 320 within the array include a plurality of overlapping boundary regions 323 between multiple adjacent recesses, creating a discrete interior recesses 321 defined by the plurality of overlapping boundary regions. The discreet interior recess 321 accordingly includes cross-sectional dimensions smaller than the expected diameter. Disruption via substantial overlap between adjacent recesses can modify one or more characteristics of the recess including, but not limited to depth, volume, curvature, slope distribution, and cross-sectional dimensions at the base.

Due at least partially to the increase in surface roughness, the engineered surfaces of the present disclosure can exhibit a minimum L* value of at least 20 at a 70 degree view angle with normally incident illumination. When used herein, view angle (i.e., scatter angle) is measured relative to the sample normal (i.e., line 164 in FIG. 3). Whiteness is an attribute of colors of high luminous reflectance and low purity, situated in a relatively small region of the color space. Lightness describes the overall intensity of the color in terms of how light or dark a color is. Under the Commission Internationale de l'Eclairage L*a*b* scoring system, the color white is distinguished by its high lightness, and surface having a perfectly white appearance has an L* of 100 (or greater if measured only at a specific view angle). Though not typically considered white, many metals have a relative high L* value when viewed at an angle substantially normal to the surface with normally incident light. As the view angle is shifted beyond 10 degrees from normal, however, the lightness decreases, resulting in a dramatic decrease in the exhibited L* value. In contrast, the L* value of the engineered surfaces according to the present disclosure can remain above 50 even as the view angle is changed from normal. In some embodiments, the L* value at a scatter angle of 30 degrees is greater than 60, in some embodiments greater than 75, and in yet other embodiments greater than 80.

In certain implementations, the engineered surfaces of the present disclosure have a reduced L* value at an incident angle normal to the surface in comparison to stainless steel. Notably, however, the reflected intensity provided by the engineered surfaces of the present disclosure does not substantially decrease as view angle changes, contributing to a relatively high L Ratio. As used herein, the "L Ratio" or "L* Ratio" is the L* value between the minimum L* value at a view angle of 70 degrees over the maximum L* value at a 15 degree view angle. A surface exhibiting a low or incalculable L Ratio can produce a dramatic change in lightness as the viewing angle or angle of incident light is rotated relative to the substantially orthogonal view, particularly when the surface is not black. Non-etched and otherwise untextured stainless steel, for example, can exhibit an L Ratio of 0. Surfaces having a moderate to high L Ratio, exhibit a more uniform lightness (i.e., L*) as a function of view angle. Engineered surfaces of present disclosure, even without aesthetic coating, can exhibit L Ratio values of at least 0.1 in some implementations, in some embodiments, at least 0.2, in some embodiments at least 0.3, in other embodiments at least 0.4, in other embodiments at least 0.6 as outlined in the Examples below.

Figure 6:
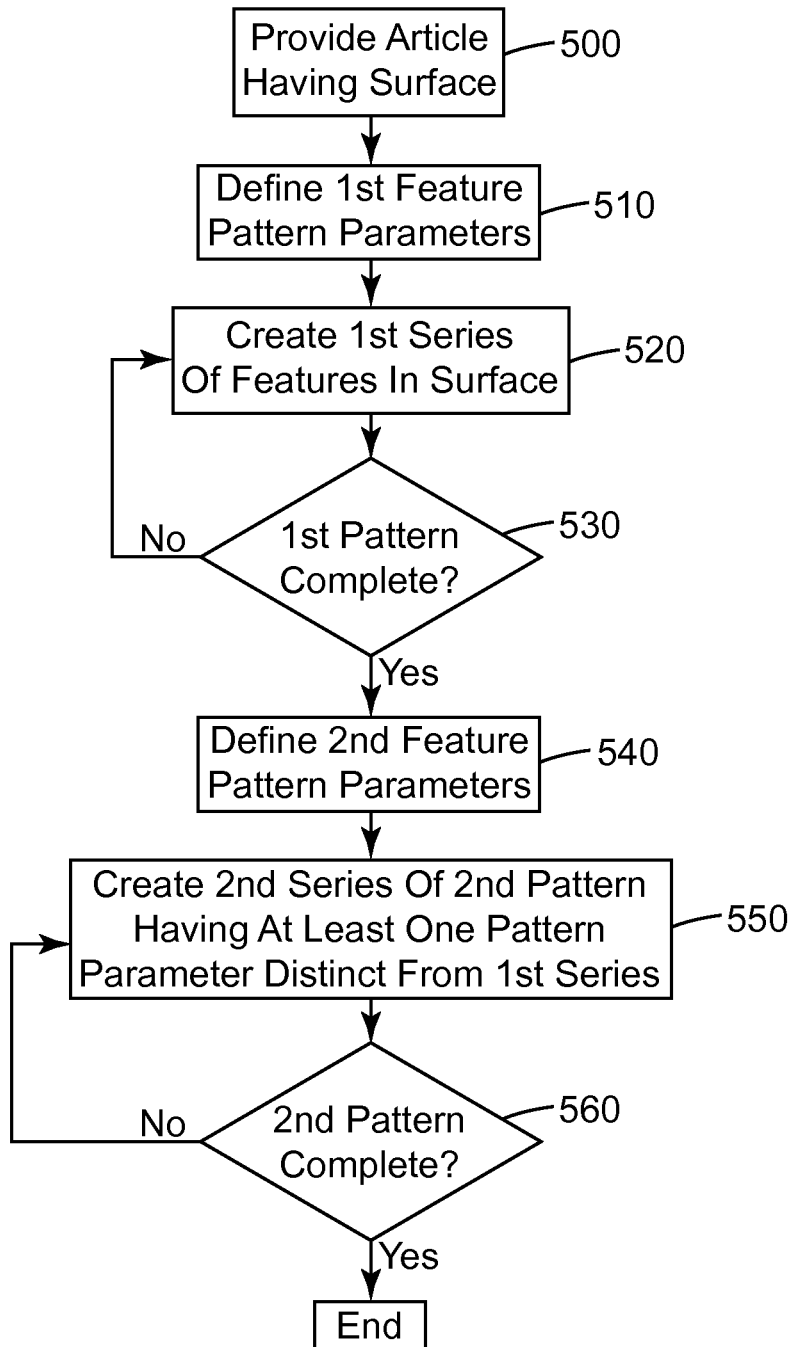
FIG. 6 is a block diagram detailing a method of creating patterns of engineered recesses on the surface of a substrate.

In another aspect, the present disclosure provides a method for creating a pattern of microscale, engineered features in a surface using laser energy. A flow diagram for this process is depicted in FIG. 6. In step 500, an article having a metal surface is provided and oriented relative to a laser source or scanner. Contaminants on the metal surface may be removed at this point, according to methods well known in the art. In step 510, laser pattern parameters relating to a first feature pattern are defined to control the initial location, spacing, and size of the ablation-created features on the surface. Relevant pattern parameters include: 1) distance (i.e., spacing) between target locations (i.e., target sites on the surface for receipt of laser energy) in both x and y directions; 2) portion or extent of the metal surface that will include engineered features; 3) laser power and/or wavelength; 4) focal point position of the laser beam relative to the substrate; and 5) repetition rate of laser energy (pulses) directed at the surface. The first feature pattern can include, but is not limited to, Cartesian grid arrays, hexagonal arrays, and other structured and unstructured arrays. Next, in step 520 the laser beam is moved across a surface of the article at a predetermined path of travel. In other implementations, the surface may be moved relative to the laser beam. During this step 520, the laser source discharges laser energy at predetermined time intervals (i.e., generates pulses) according to the determined first feature pattern parameters, thereby creating a first portion of the first feature pattern on the surface. The first portion may be a generally horizontal, vertical, diagonal, sinusoidal, spiral or other linear or non-linear series of features, depending on the first feature pattern and the desired orientation of the first feature pattern on the substrate surface. Once an initial line or series of features is created, the process proceeds to step 530, in which the laser beam is offset from the first series according to the first pattern parameters (e.g., pitch) and the laser beam proceeds to traverse the surface again at the same relative orientation between the laser beam and the substrate to create a second, subsequent portion of the first feature pattern. This process of creating pattern portions is repeated until the first pattern of engineered features is created on the desired portion of the metal surface.

Figure 9:
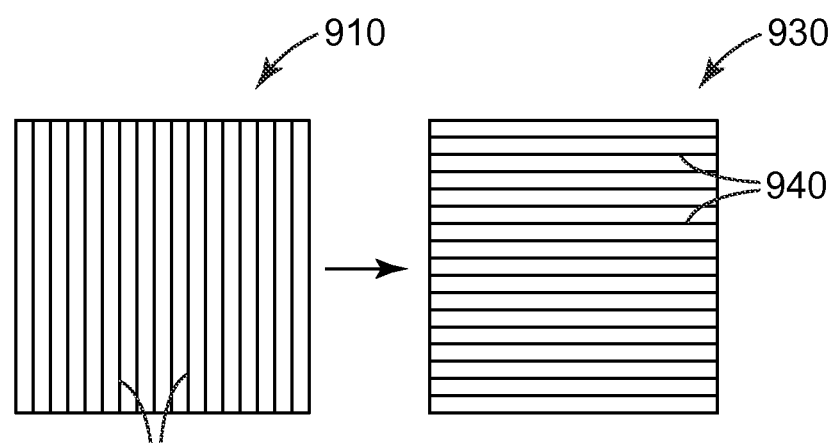
FIG. 9 is an illustration of a change in orientation of a laser pattern relative to a surface between first and second feature patterns according to an embodiment of the present disclosure.

Optionally, the process outlined in steps 500-530 may be used to create additional feature patterns that at least partially overlap with the first feature pattern as set out in steps 540-560. In presently preferred circumstances, the additional feature patterns as selected in step 540 maintain or approximate at least some of the laser pattern parameters of the first feature pattern. The orientation of the laser pattern relative to the surface can be modified, however, between or amongst feature patterns. In certain embodiments, the position of the laser beam's path of travel relative to the surface may be rotated, which results in rotation of the laser pattern. In one exemplary process depicted in FIG. 9, the laser beam travels across the surface in the y-direction in creating first feature pattern 910, resulting in series of features generally along longitudinal lines 920. Prior to creation of the second feature pattern 930, however, pattern parameters are modified such that the intended path of travel for the laser beam is rotated by 90 degrees. This rotation, as illustrated in FIG. 9, ensures that the beam will travel across the surface in the x-direction in creating the second feature pattern 930, exposing the surface to laser energy along transverse lines 940. If first and second feature pattern parameters include the same pitch in the x-direction and the same pitch in the y-direction prior to pattern rotation, the pitch of the second feature pattern in the x and y directions will be the opposite of x and y direction pitches of the first feature pattern. In other words, if the pitch between features in the first feature pattern is 20 microns in the x-direction and 25 microns in the y-direction, the rotation of the laser pattern by 90 degrees will cause the second feature pattern to include a pitch in the x-direction of 25 microns and a pitch in the y-direction of 20 microns. In alternate implementations, the surface may be rotated by, for example, 90 degrees relative to the laser beam to effectuate the same distinction in pattern parameters and/or feature spacing.

Alternatively, the second feature pattern may include a mirror of the first feature pattern, in that the pitch of the second pattern in the x-direction is the same as the pitch of the first pattern in the y-direction, for example.

Figure 14:
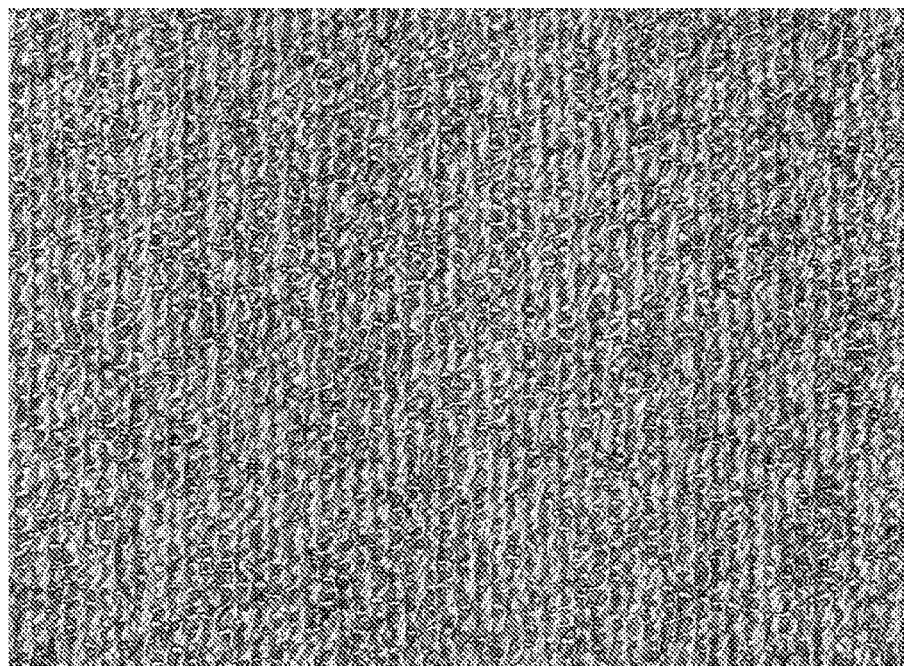
Figure 15:
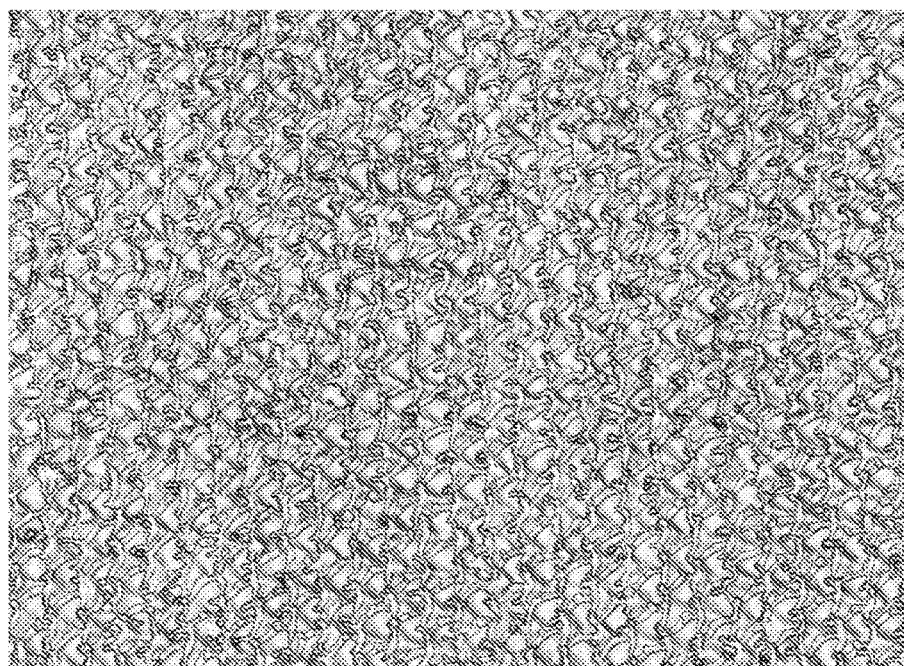
Figure 16:
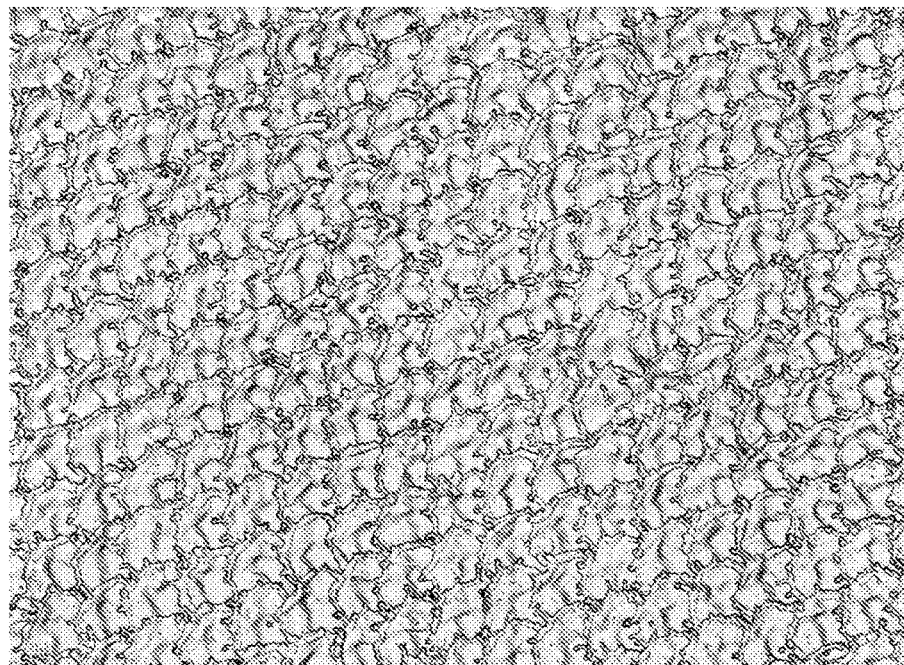
Figure 17:
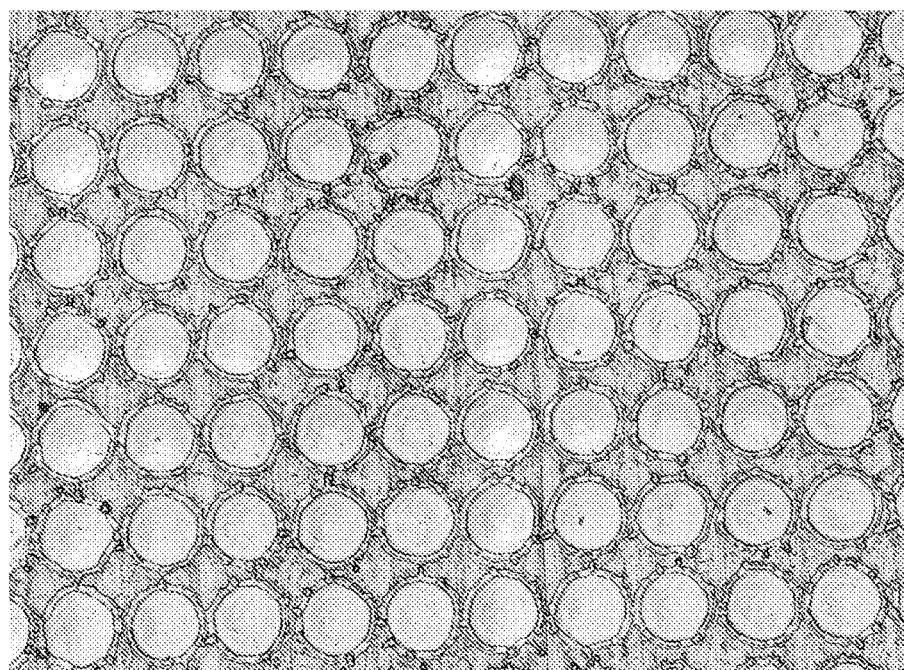
Figure 18:
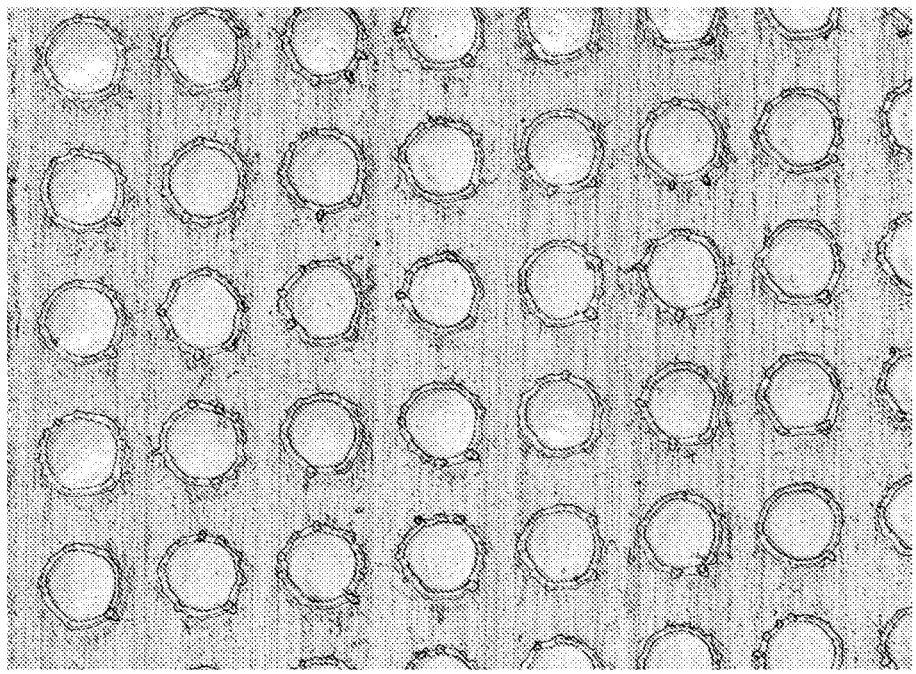
Figure 19:
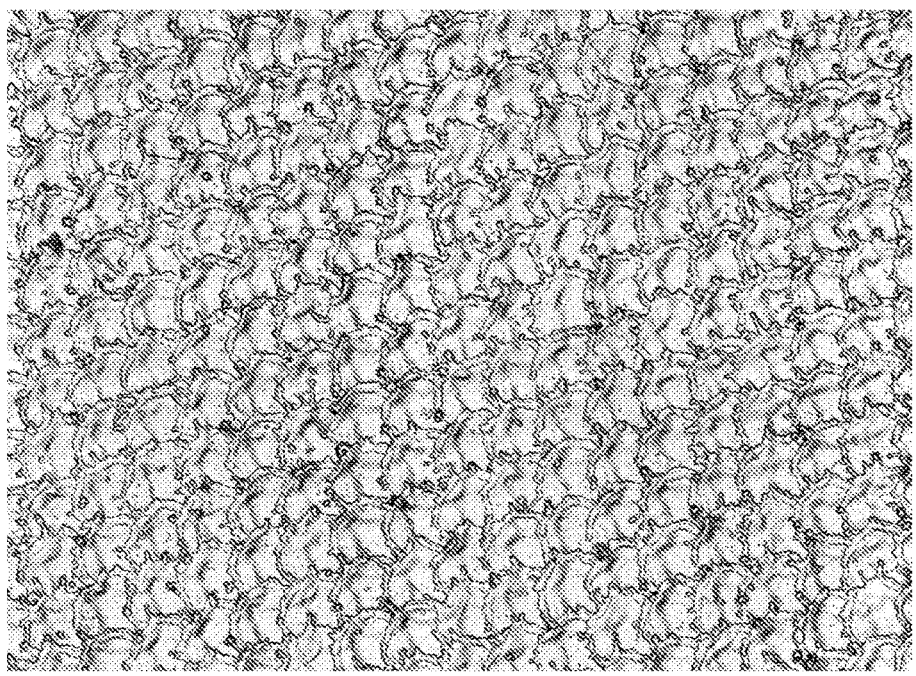
Figure 20:
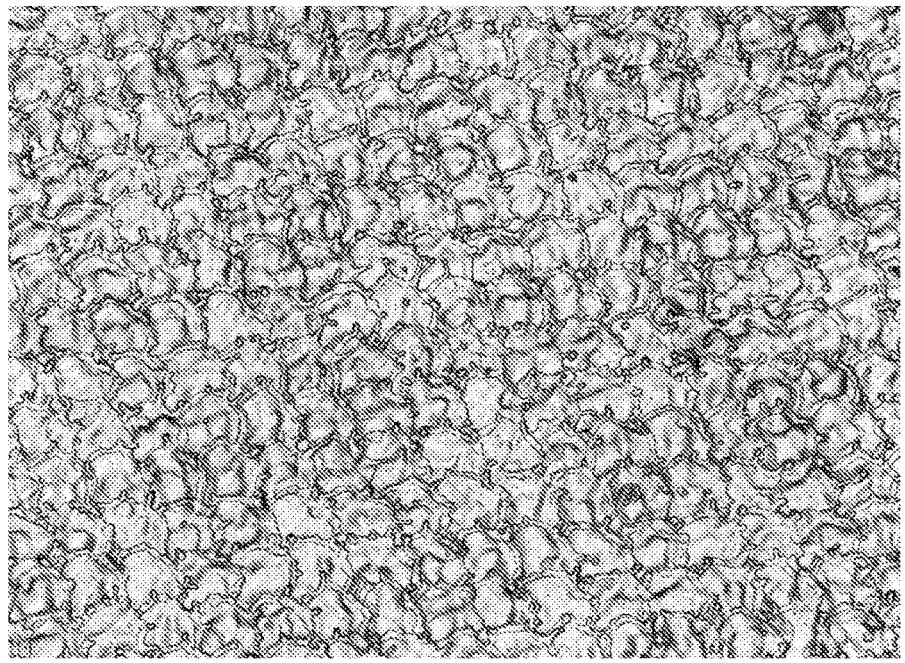
Figure 21:
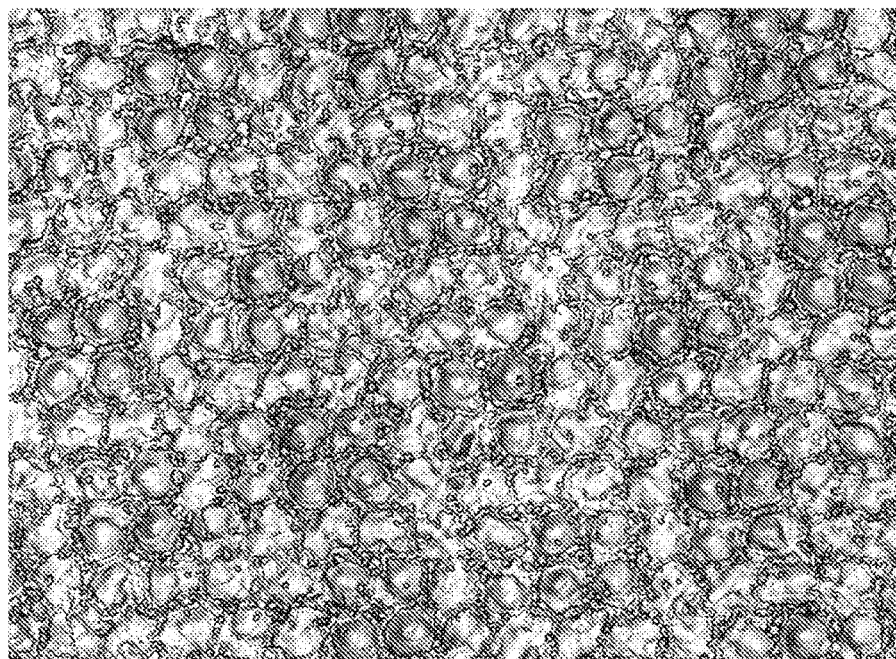

The modification in the pitch of the first and second patterns can cause significant disruption of the engineered features. In certain implementations, this disruption is caused by overlapping boundary regions of features that exceed an expected cross-sectional dimension (typically diameter). Disruption via substantial overlap between adjacent features can modify one or more characteristics of the features including, but not limited to, depth, volume, curvature, slope, slope distribution and cross-sectional dimensions at the base. Furthermore, disruption of recesses can create protrusive features in interstitial space and within the recesses. As seen in FIGS. 14 and 21 and depending on the extent of overlapping regions between adjacent features, the resulting engineered surface may appear to include aperiodic features despite any periodic character of the selected first feature pattern. Advantageously, the disruption of features can reduce gloss and other expected optical features of the metal surface, as protrusive and intrusive features account for a greater degree of diffuse reflection. The disrupted structures may still be characterized, in certain implementations, by equivalent circular diameters (ECDs) in the reference plane and by mean heights relative to the average elevation.

In other embodiments, substantial disruption may be effected with increased laser energy over the same ablation period. For example, recesses in a first feature pattern may not substantial overlap at an average power of 2.25 W. If other pattern parameters are held constant and the power is increased to, for example, 3.9 W, adjacent recesses will substantially overlap at boundary regions due to higher energy at the substrate surface. The increased energy results in a recess with a larger expected cross-sectional dimension.

If a metal or other coating is to be included on the surface of the engineered features according to methods described below, it can be advantageous to increase the expected cross-sectional dimension to a dimension greater than desired in the end state. In certain circumstances, a thickness of coating may result in a filling in of certain recesses or features, essentially flattening the surface by reducing the depth and other characteristics of features. This behavior can be countered or otherwise accommodated by adjusting the laser pattern to increase the dimension of the engineered feature.

In accounting for coating thickness, the relationship of the initial width ($w_i$) to the final width ($w_f$) of the engineered feature after depositing a coating of thickness (t) can be at least roughly determined as follows, assuming a spherical engineered feature as a part of a circular segment, with the feature width defining a chord making a central angle θ:

$$w_i = 2(R+t)\sin(0.5\theta) \quad w_f = 2R\sin(0.5\theta)$$

$$w_i = (R+t)w_f/R \text{ where } R = \text{radius of the final engineered feature.}$$

The relationship of initial depth (0 to the final depth ($d_f$) of the engineered feature after depositing a coating of thickness (t) is $$R = d_f + 0.5w_f \cot(0.5\theta) \quad R+t = d_i + 0.5w_i \cot(0.5\theta) \quad d_f = R - 0.5(4R^2 - w_f^2)^{0.5}$$

$$d_i = R+t-(R-d_f)w_i/w_f = R+t-(R-d_f)(R+t)/R$$

For example, if the desired final width and radius of the engineered recess is 30 microns and 20 microns, respectively, with 10 microns thick coating, the initial width of the engineered recess should be 45 microns. The corresponding initial depth if the final depth of the engineered feature is 6.78 microns is 10.17 microns.

Figure 7:
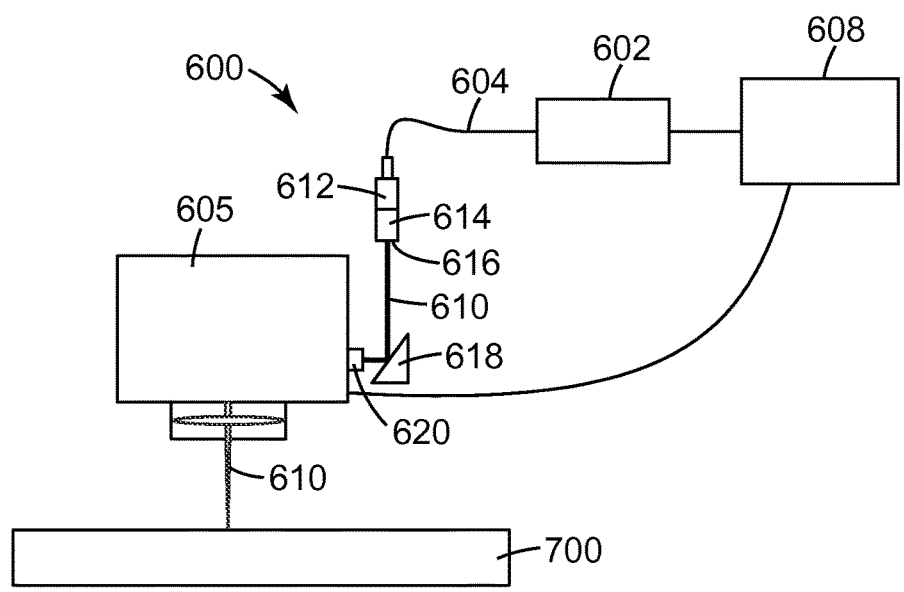
FIG. 7 is a schematic diagram of a laser ablation system according to an embodiment of the present disclosure.

In some embodiments of the method, laser energy is generated using a laser source such as, for example, a fiber laser. Laser ablation of an article surface 700 can be carried out using a laser system as depicted in FIG. 7. In some embodiments, the system 600 includes a laser source 602, a laser beam delivery fiber 604, and a controller 608. The laser source 602 is configured to generate pulses of laser energy. A moveable scanner 605, typically an optical scanner, is configured to position the laser beam 610 relative to the target location. The laser delivery fiber 604 is optically coupled to the laser source 602, and is configured to direct the laser energy 610 generated by the laser source 602 through the scanner 605 to a targeted substrate. The controller 608 is configured to control the laser source 602 and the scanner 605 based on the output signal from patterning software or direct manipulation of the scanner or substrate position by a user. The laser source 602 may comprise one or more laser sources which are used to produce the laser energy. The system 600 may also comprise conventional components, such as a beam expander 614, to produce the laser beam having the desired focal spot size. In some embodiments, the laser energy has a wavelength of approximately 532 nm (green). Other wavelengths of the laser energy 610 may also be used, such as laser energy having a wavelength of approximately 400-475 nm (blue), about 355 nm (near UV), or laser energy having a wavelength of approximately 1000-1100 nm (near IR). These and other wavelengths may be used for the laser beam 610 depending on geometries of the recesses or other features to be created in the substrate surface.

In some embodiments, the laser beam 610 generated by the laser source 602 is optically coupled to the laser beam delivery fiber 604 equipped with a conventional optical isolator 612. The laser beam delivery fiber 604 may further include any conventional optical components to shape and deliver the laser beam. The distal end of the laser fiber 604 may include optical components to discharge the laser energy 610 laterally (i.e., side-fire laser), along the axis of the laser fiber 604 (i.e., end-fire laser), or in another conventional manner. In the depicted implementation, the laser beam 610 discharged from distal end of 616 the optical isolator 612 may be directed into the scanner port 620 via mirror 618, as depicted, when the optical isolator 612 is oriented substantially perpendicular to the axis of the port 620. Such a construction can, in certain circumstances, protect the optical isolator 612 from inadvertent collisions with other components of the system. In alternative implementations, the beam 610 may be discharged parallel to the axis of port 620.

Relevant laser source parameters that may be adjusted using the controller 608 include a power level setting, a pulse width setting, a pulse repetition rate setting, and other laser source settings. In some embodiments, the controller includes or has access via network to a software program to control scan parameters (e.g., speed, angle, etc.). For example, the controller may include the LaserDESK® software program, available from SCANLAB America, St. Charles, Ill.

Figure 8A:
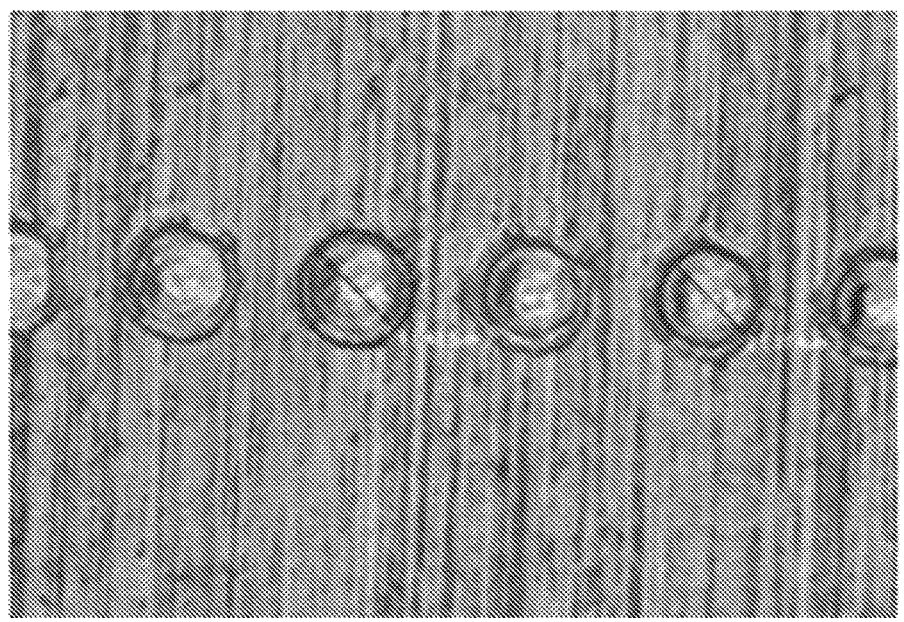
FIG. 8A is an optical micrograph of a linear series of discreet recesses according to an embodiment of the present disclosure.
Figure 8B:
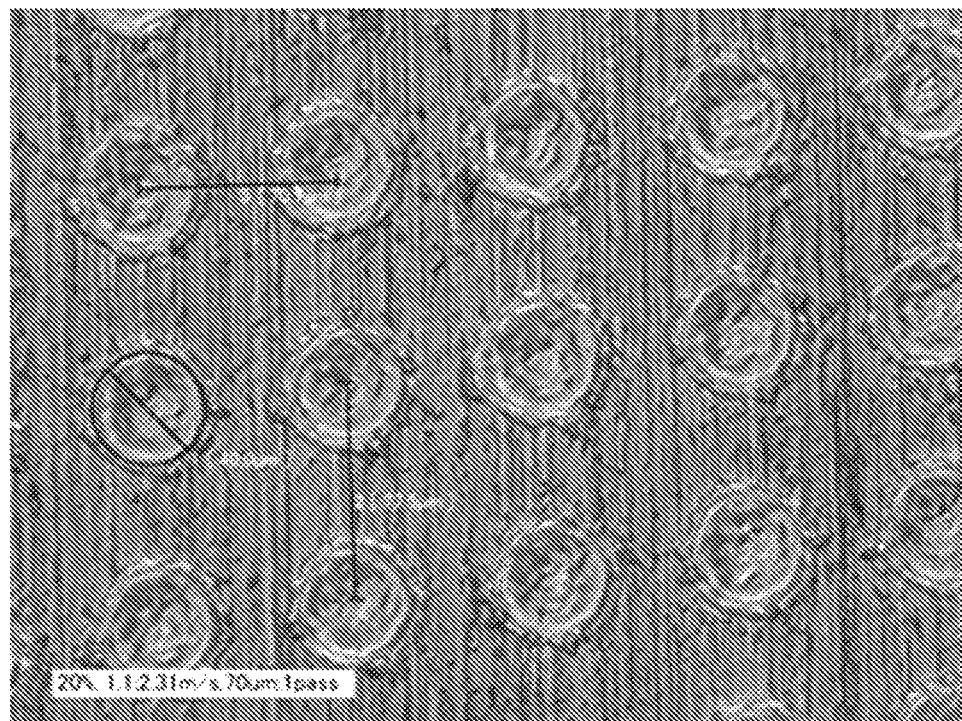
FIG. 8B is an optical micrograph of a first pattern of discreet recesses according to an embodiment of the present disclosure.

Turning again to steps 520-530, a first series of features is made along at least a portion of the metal surface (e.g., in the transverse direction) according to the selected initial spacing. The series may be created by holding the surface fixed and modifying the position of the laser beam or vice versa. In typical circumstances, a series of small recesses is created with the distance between consecutive recess dependent on the scan speed and the repetition rate of the laser.

$$d = v/f = \left[\frac{m}{s}\right]/\left[\frac{1}{s}\right] = [m] \quad \text{Equation 5}$$

where, $v$ = scan speed $d$ = recess-to-recess distance $f$ = laser repetition rate The series can form a linear array of recesses (as shown in FIG. 8A) with a pitch between adjacent recesses in the array varying from the initial feature spacing depending on the laser beam parameters selected, particularly repetition rate and scan rate. Next, a second series of recesses is created, with each recess spaced from the first according to the predetermined pitch in the y-direction. The creation of a third series of recesses is shown in FIG. 8B. The creation of additional series is repeated until the first feature pattern is complete over the desired portion of the substrate surface.

Other patterns may be created in addition to linear arrays. Recesses may be created in a sinusoidal, spiral, speckle, fractal, and myriad other patterns. In other implementations, the laser beam is aperiodically moved and fired relative to the surface.

Additional feature patterns at least partially overlapping the first feature pattern may be created in steps 540-560, typically by modifying certain pattern parameters. Though the laser patterning process illustrated in FIG. 6 only envisions the creation of two overlapping feature patterns, one skilled in the art will appreciate that any number of overlapping patterns may be created. For example, it is possible to create substantial disruption of the surface with three, four, six, and eight overlapping arrays and patterns of recesses. In presently preferred circumstances, the orientation of the laser pattern (i.e., relative position of the laser beam's path of travel) relative to the surface is modified (e.g., rotated) after the creation of each pattern.

In certain embodiments, the focal point of the laser may be adjusted to a point below the surface of the target substrate. In certain implementations the focal point is at least 50 microns below the surface of the article. In other implementations, the focal point is about 200 microns below the surface. Adjusting the focal point below the surface of the substrate can increase the size of the recesses or other features created. In other embodiments, the focal point of the laser is adjusted to be at or slightly above the surface of the article.

The creation of a pattern of microscale features can be performed in the presence of an assist gas. Although the kind of a generating gas used to perform the ablation may vary according to predetermined processing conditions, any one of argon (Ar), oxygen ($O_2$) and nitrogen ($N_2$), helium, carbon dioxide ($CO_2$), or a mixed gas of at least two thereof can be used. In presently preferred circumstances, an inert gas is used to minimize oxide formation on the ablated surface.

In alternative embodiments, an engineered surface can be formed by a variety of methods, including a variety of microreplication methods, including, but not limited to, casting, coating, and/or compressing techniques. For example, the engineered surface can be created by at least one of (1) casting a molten thermoplastic using a tool having a first feature pattern, (2) coating of a fluid onto a tool having a first feature pattern, solidifying the fluid, and removing the resulting film, (3) passing a thermoplastic film through a nip roll to compress against a tool having a first feature pattern (i.e., embossing), and/or (4) contacting a solution or dispersion of a polymer in a volatile solvent to a tool having a first feature pattern and removing the solvent, e.g., by evaporation. The tool can be formed using any of a number of techniques known to those skilled in the art, selected depending in part upon the tool material and features of the desired topography. Illustrative techniques include etching (e.g., chemical etching, mechanical etching, or other ablative means such as laser ablation, electron beam, or reactive ion etching, etc., and combinations thereof), photolithography, stereolithography, micromachining, knurling (e.g., cutting knurling or acid enhanced knurling), scoring, cutting, etc., or combinations thereof.

Alternative methods of forming an engineered surface include thermoplastic extrusion, pulsed electron beam ablation, curable fluid coating methods, and embossing thermoplastic layers, which can also be cured. Additional information regarding the substrate material and various processes for forming the engineered surface 110 can be found, for example, in Halverson et al., PCT Publication No. WO 2007/070310 and US Publication No. US 2007/0134784; US Publication No. US 2003/0235677 (Hanschen et al.); PCT Publication No. WO 2004/000569 (Graham et al.); U.S. Pat. No. 6,386,699 (Ylitalo et al.); Johnston et al., US Publication No. US 2002/0128578 and U.S. Pat. Nos. 6,420,622, 6,867,342, 7,223,364; and 7,309,519 (Scholz et al.).

As a final optional step, an aesthetic coating may be applied to an engineered surface of the present disclosure in order to further improve aesthetics. Suitable aesthetic coatings may be one of or mixture of at least two among silver (Ag), zinc (Zn), tin (Sn), indium (In), platinum (Pt), tungsten (W), nickel (Ni), chromium (Cr), aluminum (Al), palladium (Pd), gold (Au), and rhodium (Rh). Where a coating is applied to the engineered surface, it may be applied by any appropriate coating method, such as electroplating, sputtering, vapor deposition, spin coating, dip coating, roll-to-roll coating, or any other number of suitable methods. Suitable methods include those contemplated by International Publication No. WO 2009/045036 (Kim), as well as the electroplating methods for aluminum discussed in Lemkuhl et al., The Principles and Techniques of Electrolytic Aluminum Deposition and Dissolution in Organoaluminum Electrolytes in *Advances in Electrochemical Science and Engineering*, 177-226 (3d. ed., Heinz Gerischer et al., 1994) and U.S. Pat. Nos. 4,101,386 and 4,948,475 (Dotzer et al.). In certain circumstances, electroplated aluminum deposited generally according to these methods may be provided in addition to or in lieu of engineered features on the orthodontic appliance or other article.

Aesthetic metal coatings typically have a thickness in the range of about 0.1-50 microns, in some embodiments in the range of about 0.5-10 microns, and in yet other embodiments in the range of about 2-3 microns. In another embodiment, the aesthetic metal coating has a thickness of about 0.1 to 0.3 microns. Coatings having a nanoscale thickness may, in certain circumstances, more closely contour to the engineered features and result in less disruption of the desired optical effects.

In certain implementations, surface contaminants, such as oxides or nitrides, on the substrate are removed by a cleaning process before the aesthetic coating (e.g., noble metal) deposition process is initiated. Ion sputtering techniques may be used for the cleaning process. Oxides on the surface can be removed by reducing agents, such as solutions of strong acid salts or the acids themselves. Certain passive or non-platable surfaces such as stainless steel are rendered oxide free (activated) by hydrochloric acid. Shape memory alloys, such as nickel-titanium alloys, can have their surfaces activated by reducing agents, e.g., ammonium bifluoride.

Once processed to remove contaminants, the entire engineered surface can be plated by the techniques discussed above or specific areas of the engineered surface can be coated by a localized brush or small area plating device. The coating, once disposed on the engineered surface, may be anodized, passivated, or protected by barrier film according to methods known in the art.

Figure 10:
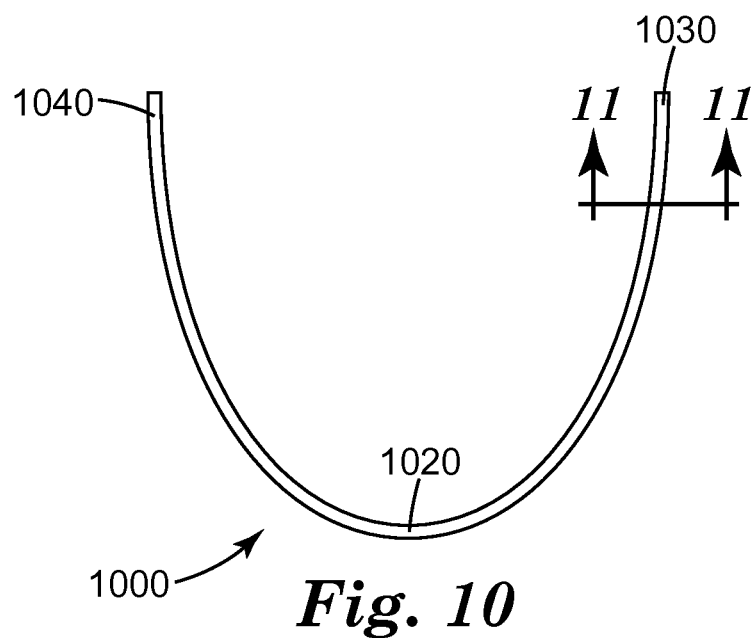
FIG. 10 is a top view of an orthodontic archwire.

Engineered surfaces of the present invention are suitable for use in myriad orthodontic and oral care applications. In one particularly advantageous implementation, an orthodontic archwire is processed to include one or more engineered surfaces. An exemplary horizontal orthodontic archwire 1000 is shown in FIG. 10 comprising a central curved portion 1020 and first and second end portions 1030, 1040 extending relative to opposing ends of central curved portion 1020.

Figure 11:
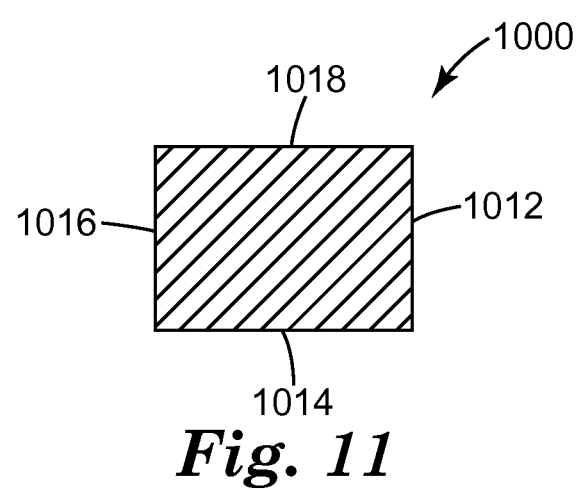
FIG. 11 is a cross-sectional view of the archwire of FIG. 10.
Figure 12:
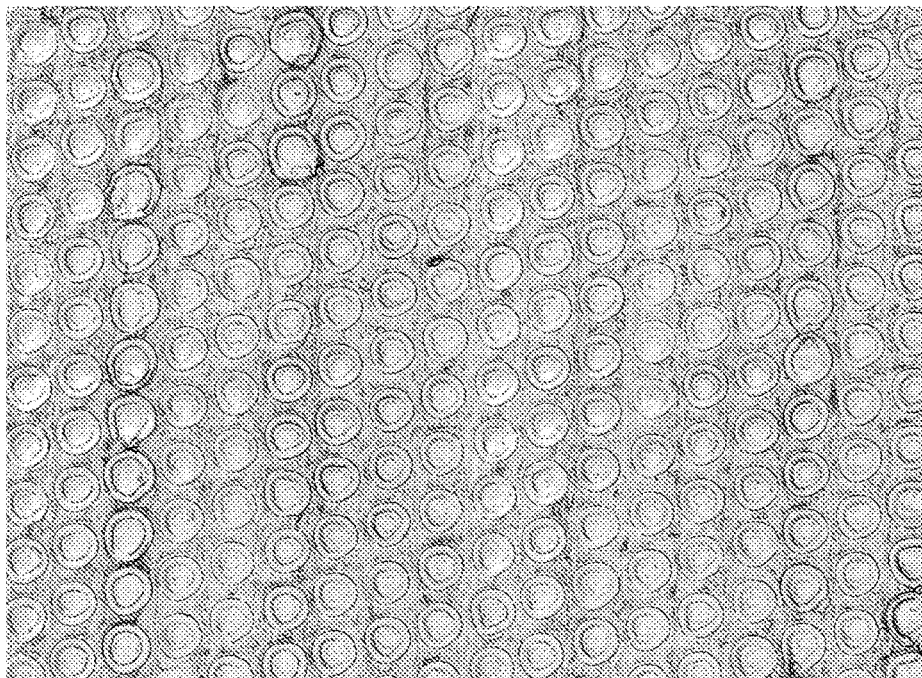
FIGS. 12-21 are laser intensity images obtained by confocal microscopy of engineered surfaces according to various embodiments of the present disclosure.
Figure 13:
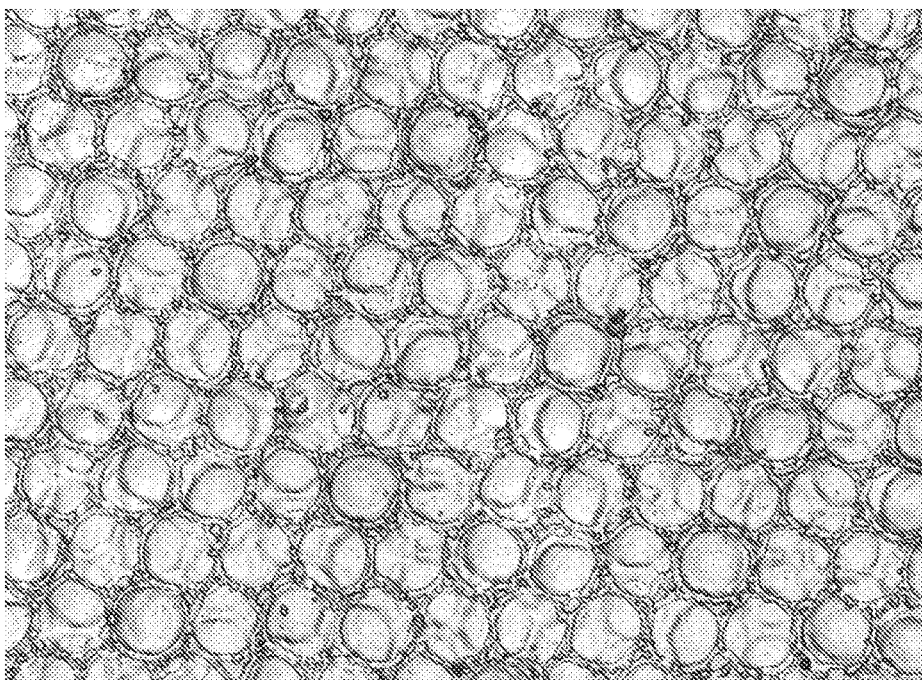

A cross-sectional view of the archwire 1000 is illustrated in FIG. 11. In this embodiment, the cross-sectional shape shown in FIG. 11 is typical of the cross-sectional shape of the archwire 1000 along its entire length. The archwire may, for example, have a generally rectangular cross-sectional shape, a circular cross-sectional shape, or an ovoid cross-sectional shape, though it will be appreciated that other cross-sectional configurations are possible. The cross-sectional shape of the archwire 1000 is typically substantially uniform along its entire length. However, other embodiments are possible, such as archwires wherein the cross-sectional shape of the archwire varies from one portion to the next along the length of the archwire.

The four sides 1012, 1014, 1016, 1018 of the exemplary cross-sectional shape of the archwire 1000 as shown in FIG. 11 present a rectangle. The occlusal side 1014 and the gingival side 1018 are generally flat and parallel to each other, and the buccolabial side 1012 and the lingual side 1016 are flat and parallel to each other. The distance between the sides 1014, 1018 is typically selected to matingly fit within an archwire slot or passage of an orthodontic appliance such as a bracket or buccal tube. It will be appreciated by those skilled in the art that the identification of the occlusal and gingival sides will depend on whether the archwire is installed on the upper or lower dental arch.

In some embodiments, all four sides are ablated or otherwise treated to include an engineered surface. In other implementations, only three sides include an aesthetic, engineered surface. For example, only the buccolabial 1012, occlusal 1014, and gingival sides 1018 may include an engineered surface, with the lingual surface 1016 untreated. In yet other implementations, only the buccolabial surface 1012 is treated to include the engineered surfaces of the present disclosure, In some embodiments, only the central portion 1020 includes the engineered surfaces of the present disclosure. In other embodiments, the central portion 1020 and one or both the end portions 1030, 1040 include engineered surfaces.

In another embodiments an engineered surface may be created on myriad dental and orthodontic components, including but not limited to orthodontic brackets, buccal tubes, archwire slot liners, self-ligating clips and other latches, restoratives, replacements, inlays, onlays, veneers, full and partial crowns, bridges, implants, implant abutments, copings, anterior fillings, posterior fillings, and cavity liners, and bridge frameworks.

Embodiments

1. An orthodontic appliance comprising: an exterior surface including metal; and a plurality of recesses in the exterior surface, and wherein the surface including the plurality of recesses exhibits a Total CIE Chroma of no greater than 14 and a minimum L* value of at least 20 at an incident angle of 0 degrees and a view angle of 70 degrees, as measured by the Diffuse Scattering Test.
2. The orthodontic appliance of embodiment 1, wherein the shape of at least one recess is concave.
3. The orthodontic appliance of embodiment 2, wherein the average depth of the plurality of recesses is at least 0.5 microns and no greater than 20 microns.
4. The orthodontic appliance of embodiment 1, wherein the pitch between adjacent recesses array is at least 15 microns and no greater than 60 microns.
5. The orthodontic appliance of embodiment 4, wherein the pitch between adjacent recesses within an array is at least 20 microns and no greater than 40 microns.
6. The orthodontic appliance of embodiments 4-5, wherein the recesses are arranged in an array having a transverse axis and a longitudinal axis, and wherein the pitch between adjacent recesses along the transverse axis is greater than a pitch between adjacent recesses along the longitudinal axis.
7. The orthodontic appliance of embodiment 1, wherein each recess of the plurality of recesses includes a base having a cross-sectional dimension, and wherein the dimension is at least 5 and no greater than 60 microns.
8. The orthodontic appliance of embodiment 7, wherein the cross-sectional dimension includes a diameter, and wherein the diameter is at least 20 and no greater than 40 microns.
9. The orthodontic appliance of embodiment 8, wherein the diameter of the base is greater than the pitch.
10. The orthodontic appliance of embodiment 8, wherein the diameter is at least 25 and no greater than 35 microns, and wherein the pitch is at least 25 and no greater than 35 microns.
11. The orthodontic appliance of any of the previous embodiments, wherein the ratio between the average depth of the recesses and the average cross-sectional dimension at the base of the recesses is at least 1:1.5.
12. The orthodontic appliance of any of the previous embodiments, wherein the ratio between the average depth of the recesses and the average cross-sectional dimension at the base of the recesses is at least 1:2.
13. The orthodontic appliance of embodiment 1, wherein at least two recesses of the plurality of recesses are arranged in a periodic array.
14. The orthodontic appliance of embodiment 13, wherein the boundary regions of any two recesses in the linear array do not substantially overlap.
15. The orthodontic appliance of embodiment 14, wherein the surface includes interstitial space between any two recesses in an array.
16. The orthodontic appliance of embodiment 15, wherein the interstitial space between recesses is substantially planar.
17. The orthodontic appliance of embodiment 15, wherein the interstitial space between recesses include one or more protrusive features.
18. The orthodontic appliance of embodiment 13, wherein at least one recess includes, protrusive features on a bottom surface of the recess.
19. The orthodontic appliance of embodiment 1, wherein the recesses are arranged in a periodic array of concave wells, wherein each well includes a base at least partially defined by the surface, and wherein each base includes a greatest dimension of at least 20 microns and no greater than 50 microns.
20. The orthodontic appliance of embodiment 1, wherein the recessed surface exhibits a minimum L* value of at least 30.
21. The orthodontic appliance of embodiment 20, wherein the recessed surface exhibits a minimum L* value of at least 50.
22. The orthodontic appliance of embodiment 21, wherein the recessed surface exhibits a minimum L* value of at least 60.
23. The orthodontic appliance of embodiment 1, wherein the surface includes at least two arrays, each array including a plurality of recesses, and wherein the recesses are aperiodically disposed over a portion of the surface.
24. The orthodontic appliance of any of the previous embodiments, wherein the appliance is an archwire.
25. The orthodontic appliance of any of the previous embodiments, wherein the appliance comprises an orthodontic clip.
26. The orthodontic appliance of any of the previous embodiments, wherein the appliance comprises a base and a body extending outwardly from the base, the body defining an elongated slot, and wherein the engineered surface is disposed on at least a portion of the body.
27. An appliance comprising: a body having an exterior surface including metal; and a plurality of engineered features on the surface, the surface exhibiting a diffuse L* min70/max15 ratio of at least 0.2 at a Total CIE Chroma of less than 14, a minimum L* value of at least 20 at an incident angle of 0 degrees and a view angle of 70 degrees, as measured by the Diffuse Scattering Test.
28. An appliance according to embodiment 24, wherein the surface exhibits a diffuse L* min70/max15 ratio of at least 0.4, as measured by the Diffuse Scattering Test.
29. An appliance according to the previous embodiment, wherein the surface exhibits a diffuse L* min70/max15 ratio of at least 0.5, as measured by the Diffuse Scattering Test.
30. The appliance of any of the previous embodiments, wherein the surface exhibits the diffuse L* min70/max15 ratio in the absence of any aesthetic coating.
31. An appliance comprising: an exterior surface including a metal; a plurality of recesses defined in the surface, each recess having a depth from the surface of at least 0.5 microns, wherein the recesses are arranged in overlapping arrays such that a majority of the recesses overlap with adjacent recesses at boundary regions.
32. The appliance of embodiment 31, wherein the at least one recesses of the plurality of recesses is arranged in a unit cell with at least one other recess, and wherein the pitch between recesses in the unit cell is at least 20 microns and no greater than 50 microns.
33. The appliance of embodiment 32, wherein the pitch between adjacent recesses within a unit cell is at least 25 microns and no greater than 40 microns.
34. The appliance of embodiment 32, wherein at least a portion of the surface between any adjacent recesses in a unit cell is substantially planar.
35. The appliance of embodiment 31, wherein the overlapping boundary regions include a series of discreet protrusive features in the surface.
36. The appliance of any of the previous embodiments, wherein the surface exhibits a diffuse L* min70/max15 ratio of at least 0.4, as measured by the Diffuse Scattering Test.

37. The appliance of any of the previous embodiments, wherein the surface exhibits a diffuse L* min70/max15 ratio of at least 0.6, as measured by the Diffuse Scattering Test.
38. The appliance of embodiment 26, wherein the surface exhibits a minimum L* value of at least 50 at a 70 degree view angle as measured by the Diffuse Scattering Test.
39. The appliance of any of the previous embodiments, wherein at least one recess includes a depth of about 10 microns.
40. A method for improving the aesthetic appearance of an article, the method comprising: providing an article having an exterior surface, the surface including metal; ablating at least a portion of the surface to create a plurality of features thereon, such that the surface exhibits a diffuse L* min70/max15 ratio of at least 0.2, as measured by the Diffuse Scattering Test.
41. The method of the previous embodiment, wherein the plurality of features comprise a plurality of recesses in the surface.
42. The method of embodiment 40, wherein at least some of the recesses overlap to form protrusive features.
43. The method of any of the previous embodiments, wherein the recesses are periodically arranged on the surface.
44. The method of embodiment 43, wherein the area of the surface between adjacent recesses includes protrusive features.
45. The method of any of the previous embodiments, wherein ablating at least a portion of the surface includes creating a first pattern of recesses, the first pattern having a pitch between adjacent recesses in the array of at least 10 microns and no greater than 100 microns.
46. The method of embodiment 45, wherein the first pattern includes a pitch between adjacent recesses in the pattern of at least 20 microns and no greater than 60 microns.
47. The method of embodiment 45, wherein the recesses are arranged in an array having a transverse axis and a longitudinal axis, and wherein the pitch between adjacent recesses along the transverse axis is greater than a pitch between adjacent recesses along the longitudinal axis.
48. The method of any embodiment 44, wherein the first pattern of recesses is arranged in a grid array, the grid having vertical and horizontal spacing between adjacent recesses, wherein the horizontal spacing is different than the vertical spacing.
49. The method of embodiments 47 or 48, wherein the horizontal spacing is greater than the vertical spacing.
50. The method of any of the preceding embodiments, wherein ablating a portion of the surface further includes creating a series of recesses according to a second pattern, wherein the second pattern is substantially similar to the first pattern.
51. The method of any of the previous embodiments, wherein ablating the surface comprises periodically exposing the surface to the beam of a laser.
52. The method of embodiment 51, wherein the laser beam has pulse duration of 0.1-500 ns and periodically interacts with the surface.
53. The method of embodiment 51, wherein ablating the surface includes selecting a focal point for a laser relative to the surface, and wherein the focal point is above or below the surface of the article.
54. The method of embodiment 53, wherein the focal point is at least 100 microns below the surface of the article.
55. The method of embodiment 54, wherein the focal point is about 200 microns below the surface.
56. The method of any of the previous embodiments, wherein the article is an orthodontic archwire.
57. The method of embodiment 56, wherein the step of providing the article includes the act of unwinding the archwire from a spool.
58. The method of any of the previous embodiments, wherein the article is a clip having at least one recess for receiving an archwire.
59. The method of any of the previous embodiments, wherein the features include discreet recesses and elongated protrusions, wherein the protrusions are aperiodically arranged between discreet recesses.
60. The method of embodiment 59, wherein the discreet recesses include a concave lens-like structure, and the wherein the recesses include discrete protrusive features proximate an apex of the lens.
61. The method of any of the previous embodiments, wherein ablating the surface includes creating a first pattern of features in a first array over at least a portion of the surface, and disrupting a portion of the first pattern, such that the geometric dimension of at least two recesses of the first pattern is changed.
62. The method of embodiment 61, wherein disrupting a portion of the first pattern comprises creating a second pattern of features in a second array, wherein the second pattern of features is offset from the first pattern and wherein the features of the second array at least partially overlap with features of the first array.
63. The method of embodiment 61, wherein ablating the surface comprises periodically exposing the surface to laser energy at a first pattern orientation; modifying the laser path of travel relative to the surface to define a second pattern orientation; and periodically exposing the surface to laser energy at the second pattern orientation.
64. The method of embodiment 63, wherein the second orientation is orthogonal to the first orientation.
65. The method of embodiment 63, wherein second orientation represents an angular rotation from the first orientation, and wherein the angular rotation includes an oblique angle.
66. The method of any of the previous embodiments, wherein ablating the surfaces is performed in the presence of inert gas.
67. The method of any of the previous embodiments, wherein the metal includes at least one of stainless steel, aluminum, titanium, beta-titanium, nickel titanium, and alloys thereof.
68. The method of any of the previous embodiments, wherein the surface exhibits a diffuse L* min70/max15 ratio of at least 0.2, and a minimum L* value of at least 20 an incident angle of 0 degrees and a view angle of 70 degrees, as measured by the Diffuse Scattering Test.
69. The method of any of the previous embodiments, wherein the surface exhibits a diffuse L* min70/max15 ratio of at least 0.4, as measured by the Diffuse Scattering Test.
70. The method of embodiment 68 or 69, wherein the surface exhibits the diffuse L* min70/max15 ratio in the absence of any aesthetic metal or polymeric coating.
71. The method of the previous embodiments, wherein the surface exhibits a Total CIE Chroma of no greater than 14 and a minimum L* value of at least 20 an incident angle of 0 degrees and a view angle of 70 degrees, as measured by the Diffuse Scattering Test.
72. The method of embodiment 71, wherein the surface exhibits a Total CIE Chroma of no greater than 14 and a minimum L* value of at least 50 at an incident angle of 0 degrees and a view angle of 70 degrees, as measured by the Diffuse Scattering Test.

73. An orthodontic appliance comprising:
an exterior surface including metal; and an electroplated metal coating on the exterior surface, and wherein the coated surface exhibits a Total CIE Chroma of no greater than 14 and a minimum L* value of at least 20 at an incident angle of 0 degrees and a view angle of 70 degrees, as measured by the Diffuse Scattering Test.

74. The orthodontic appliance of embodiment 73, wherein the appliance is an orthodontic archwire.

75. The orthodontic appliance of embodiment 73 or 74, wherein the electroplated metal coating comprises at least one of aluminum and rhodium.

Advantages of this disclosure are further illustrated by the following examples, but the particular materials and amounts thereof recited in these examples, as well as other conditions and details, should not be construed to unduly limit this invention. Unless otherwise indicated, all parts and percentages are by weight.

EXAMPLES

As more fully described below, a variety of metal substrates were subjected to laser ablation processes such that the laser processed substrates generally displayed a white, non-glinting appearance, in contrast to typical metal surfaces. While not wishing to be bound by any particular theory, it is believed that these desirable optical effects are the result of surface textures created in the laser ablation process. In particular, the textured surfaces display reduced specular reflection and increased diffuse reflection of incident light, such that the "glare" commonly observed with typical metal surfaces is greatly reduced and the surface is demonstrably whiter at a wider range of viewing angles.

Sample Creation
Laser Setup

Experiments were performed with a 40 W pulsed fiber laser operating at a wavelength of 1061 nm (available from SPI Lasers, Southampton (UK), Part number SP-40P-0508-001), with a beam quality factor ($M^2$) of ~3.15. The laser was protected from back reflection with a Faraday optical isolator mounted at the end of the beam delivery fiber. Parameters such as power, pulse duration, and repetition rate were variable. Table 1 shows the preconfigured electrical pulse durations for the 40 W pulsed fiber laser. The electrical pulse duration should be substantially similar to the actual, optical pulse of the laser.

TABLE 1

| Waveform Number, WFM | 40 W Pulsed Laser Electrical Duration (ns) | 40 W Pulsed Laser Repetition Rate (kHz)/Maximum Pulse Energy (mJ) |
| --- | --- | --- |
| 0 | ~250 | 30/1.33 |
| 1 | ~130 | 47/0.85 |
| 2 | ~60 | 76/0.53 |
| 3 | ~30 | 145/0.28 |
| 4 | ~20 | 230/0.17 |
| 5 | ~9 | 250/0.16 |

The laser beam was directed to a commercially available 2D galvo laser scanner head (hurrySCAN® 20, available from ScanLab America, Inc., Naperville, Ill.) equipped with a 100 mm telecentric f-theta focusing lens. The scanner was mounted to a 3D gantry system (available from Aerotech, Inc., Pittsburgh, Pa.) to enable positioning in the X, Y, and Z directions in the laser patterning process further described below. An exhaust system (FA-2, available from Fumex, Inc., Kennesaw, Ga.) was used to minimize contamination of the work area with local debris. In some instances, a local assist gas of compressed nitrogen (volumetric flow rate of ~140 L/min) was used to prevent oxidation of the laser patterned surface (particularly at higher laser powers) as well as to keep local debris from entering the work area.

The beam was expanded with a 7× beam expander enlarging the beam diameter from approximately 1.1 mm to approximately 7.7 mm before entering the scanner. Images of the processed substrates were recorded with a microscope (VHX-2000, available from Keyence Corp., Itasca, Ill.) capable of high magnification and microscopic measurements. A block diagram of the fiber laser system is shown in FIG. 7.

Substrates

Rectangular, metal shim stock coupons (~0.33-0.39 mm—~12.7 mm—~50.8 mm) of 304 and 316 stainless steel ("304SS" and "316SS", available from Xylem Co., Inc., Chanhassen, Minn.) or nitinol ("NiTi", Nitinol Devices & Components, Inc., Fremont, Calif.) were used as substrates in the laser patterning experiments. The substrates were clamped to the process platform via a magnetic chuck prior to laser patterning. A small square portion (~10 mm×10 mm) of the coupon was patterned according to parameters outlined below. After patterning, the substrates were cleaned in an ultrasonic acid bath.

Laser Patterning Parameters
I. Single Pass Patterning

Examples S1, S3-S7, S10 and S12 employed NiTi or 304SS coupons as substrates. The substrates were laser patterned with a series of approximately parallel "lines" using LaserDESK software (ScanLab AG) to design the pattern, with each "line" being composed of a linear series of concave-shaped features on the patterned surface. An illustration of such "lines" extending in the transverse direction on an article surface is shown in FIG. 8A. During patterning, the distance between adjacent features within a given "line" was a function of both the scan speed and the repetition rate of the laser. The relationship between the scan speed of the laser beam, repetition rate, and the distance between adjacent features is shown in Equation 5, where v is the scan speed, d is the feature-to-feature distance, and $f$ is the laser repetition rate.

$$d = v/f = \left[\frac{m}{s}\right] / \left[\frac{1}{s}\right] = [m] \qquad \text{Equation 5}$$

The size of the feature is dependent on the diameter of the beam entering the focusing optics (the f-theta lens), the beam quality factor, and pulse energy (laser power). Thus, the feature size could be easily varied. FIG. 8A shows a 1000× magnified image of a 304SS surface patterned with a single line (i.e., series) of recesses created using the 40 W fiber laser at 2.25 W, with a line scan speed of 1 m/s a repetition rate of 30 kHz, and a waveform of 0 (pulse duration ~250 ns). From the experimentally determined feature size, various feature-to-feature distances were evaluated for their effect on the optical characteristics of the patterned surface.

Initial observations revealed that, under certain parameters, single pass patterning provides sample substrates where the surface is not sufficiently white at the desired wide range of viewing angles. This suggested that, for certain applications, further patterning and feature disruption might be desirable.

II. Two Pass Patterning

Two pass patterns were created on the 304SS and NiTi coupons of Examples S2, S8, S9, S11, and S13 as follows. A ~10 mm×10 mm portion of each Example substrate was patterned with as series of parallel lines, the laser pattern rotated by 90°, and the patterning process repeated over the same ~10 mm×10 mm portion. FIG. 9 illustrates a two pass patterning sequence, with a 90° rotation of the laser pattern between passes (only the engineered portion of the substrate is illustrated). The initial "lines" 920 of the first feature pattern 910 extend in the longitudinal direction on an article surface 900 prior to rotation. As the pattern is rotated 90 degrees and the laser beam path of travel changed, the series of "lines" 940 of the second pattern 930 extend in the transverse direction.

In general, a spacing ratio was selected and the corresponding feature-to-feature distance was calculated depending on the desired pitch and a scan speed arrived at by multiplying by the repetition rate of the laser shown in Equation 5. A spacing ratio of 1.1 and pitch of 30 μm are used in the calculations shown below:

$$d = 1.1 \times 30 \; [\mu m] =$$ Equation 5

-continued $$33\left[\frac{\mu m}{pulse}\right] \rightarrow v = 33\left[\frac{\mu m}{pulse}\right] \times 30{,}000\left[\frac{pulse}{sec}\right] = 0.99\left[\frac{m}{s}\right]$$

A summary of the 2-pass laser patterning parameters are shown in Table 2.

TABLE 2

| Number of passes | 2 |
|---|---|
| Rotation between passes (°) | 90 |
| Waveform | 0 |
| Repetition Rate (kHz) | 30 |
| Energy (W) | 3.9 |
| Scan speed (m/s) | 1 |

The LaserDESK software used to control the scanner included pertinent parameters such as scan speed, pitch, laser delays, and jump speeds between scanning, with the pitch and derived scan speed as the variable inputs. Feature size (e.g., diameter, ECD, and depth) can be varied according to the power of the laser. In certain instances, neighboring features are so closely packed, that noticeable interference (i.e., overlapping feature boundary regions) is evident, shrinking the effective feature diameter or ECD.

Table 3 shows a summary of the samples S1-S21 tested during the course of experiments. All patterned samples included a spacing ratio of 1.1:1. Pitch in the x-direction of the first pattern is reported first in Table 3.

TABLE 3

| Samples S1-S18 | | | | | |
|---|---|---|---|---|---|
| Sample | Substrate | Laser Patterned? | Laser Pattern Parameters/ Other Description | Coating (thickness) | Corresponding FIG. |
| S1 | 304SS | Yes | 1 pass, 33 × 30 μm pitch, 2.25 W | None | 12 |
| S2 | 304SS | Yes | 2 passes, 44 × 40 μm pitch, 3.9 W | None | 13 |
| S3 | 304SS | Yes | 1 pass, 11 × 10 μm pitch, 3.9 W | None | 14 |
| S4 | 304SS | Yes | 1 pass, 22 × 20 μm pitch, 3.9 W | None | 15 |
| S5 | 304SS | Yes | 1 pass, 33 × 30 μm pitch, 3.9 W | None | 16 |
| S6 | 304SS | Yes | 1 pass, 55 × 50 μm pitch, 3.9 W | None | 17 |
| S7 | 304SS | Yes | 1 pass, 77 × 70 μm pitch, 3.9 W | None | 18 |
| S8 | 304SS | Yes | 2 passes, 33 × 30 μm pitch, 3.25 W | Rh (~0.4 μm) | 19 |
| S9 | 304SS | Yes | 2 passes, 33 × 30 μm pitch, 3.25 W | Rh (~2.0 μm) | |
| S10 | 304SS | Yes | 1 pass, 33 × 30 μm pitch, 3.25 W | Al (~75 nm) | 20 |
| S11 | 304SS | Yes | 2 passes, 33 × 30 μm pitch, 3.25 W | Al (~75 nm) | 21 |
| S12 | 304SS | Yes | 1 pass, 33 × 30 μm pitch, 3.25 W | Al (~150 nm) | |
| S13 | 304SS | Yes | 2 passes, 30 μm pitch, 3.25 W | Al (~150 nm) | |
| S14 | 304SS | No | Electoetched for 5 min, 5 V in 10% chromic acid with a current of 2.3 A, followed by Al coating. | Al (~150 nm) | |
| S15 | Matte Nickel | No | Matte nickel coupon (~1.5 mm × ~17.8 mm × ~25.4 mm) prepared by electroplating Ni onto a SS substrate, then removing the deposited matte nickel layer from the SS substrate, followed by Al coating. | Al (~150 nm) | |
| S16 | NiTi | No | Electoetched for 5 min, 5 V in methanol:sulfuric acid (4:1) with a current of 0.3 A, followed by Al coating. | Al (~150 nm) | |
| S17 | 304SS | No | — | Al (~150 nm) | |
| S18 | Human Tooth (incisor) | No | — | — | |
| S19 | NiTi | No | Electroplated with Al, generally according to U.S. Pat No. 4,948,475 | Al (12 μm) AlO$_x$ (5 μm) | |
| S20 | 304SS | No | Electroplated with Al, generally according to U.S. Pat No. 4,948,475 | Al (12 μm) AlO$_x$ (5 μm) | |
| S21 | 316SS | No | Electroplated with Al, generally according to U.S. Pat No. 4,948,475 | Al (20 μm) | |

Surface Coatings

In Examples S8-S17, the patterned substrates were further subjected to a metal coating process (after ultrasonic cleaning) to further enhance optical and other qualities. Aluminum (Al) coatings (~75 nm or ~150 nm thickness) were applied to selected patterned substrates (S10-S17) using an e-beam/thermal evaporator (K. J. Lesker Co., Jefferson Hills, Pa.). Aluminum was deposited at a rate of 15 angstroms per second in the absence of an external gas at a chamber pressure of approximately $3 \times 10^{-5}$ Torr. Aluminum (AL) coatings (~5-20 µm thickness) were applied to unpatterned substrates (S19-S21) using electroplating methods generally described in Lemkuhl et al., The Principles and Techniques of Electrolytic Aluminum Deposition and Dissolution in Organoaluminum Electrolytes in *Advances in Electrochemical Science and Engineering*, 177, 204-211 (3d. ed., Heinz Gerischer et al., 1994), as well as U.S. Pat. Nos. 4,101,386 and 4,948,475 (Dotzer et al.). Rhodium (Rh) coatings (~0.4-2.0 µm thickness) were also applied via conventional electroplating (Prodigy Surface Tech., Santa Clara, Calif.).

Optical Measurements

Gloss Measurements

Gloss, as used herein, is the ability of a surface to reflect visible light in specular directions. Gloss measurements were made using a Novo-Curve Gloss Meter (Rhopoint Instruments, East Sussex, UK) at an incident angle of 60 degrees and conformed to standard test methods (ASTM D523, ISO 2813, DIN 67530, and JIS Z 8741). Reported results are an average of two measurements for given sample, with the sample being rotated 90 degrees between measurements.

Diffuse Scattering Test

Color bidirectional scattering distribution function (BRDF) measurements were obtained with an IS-SA Imaging Sphere (available from Radiant Vision Systems, Redmond, Wash.) using the following settings: Incidence Angles: 0°; Binning 1×1; Color: XYZ color; ND filter: 100%; Aperture: (6 mm S1-S18, 10 mm S19-S21); Beam size: smallest setting; Hole fill: on; Force Dark Exposure: on; Exposure Setting: bright spot; Saturation: 75%; Data Export resolution: 2°. Samples were secured to the aperture.

In all cases BRDFs were measured for each sample at an incidence angle of 0° with specular light excluded. Color measurements were made based on the Commission Internationale de l'Eclairage L*a*b* scoring system. The CIE L* and total CIE chroma were calculated along the vertical and horizontal cross sections of the 0° incidence BRDFs. The total CIE chroma is equal to the root mean square of the total CIE a* and total CIE b* and is the distance in color space from the L* axis. It represents the color saturation; a zero chroma has no color. A perfect Lambertian reflector was chosen to be the reference white which has a BRDF equal to $1/\pi$ for all incidence and scattered (i.e., view) angles. From exported data, the minimum and maximum CIE L* were also calculated as a function of view angle. CIE L* can vary as a function of azimuthal angle. The minimum and maximum CIE L* were accordingly calculated over all the azimuthal angles for each given view angle. Note that because the measured CIE L* is only for a specific view angle, it is possible for it to be greater than 100. Due to asymmetry in the scatter pattern, it was instructive to look at the minimum and maximum CIE L* as a function of view angle instead of a total integrated value.

Confocal Scanning Laser Microscopy (CSLM)

Representative samples were characterized using confocal scanning laser microscopy (50× objective). A Keyence VK-9710 (available from Keyence Corporation of America, Itasca, Ill.) was used for samples S1-S17 with the following settings: Real Peak Detection (RPD): on Mode: surface profile; Area: plane; Quality: super fine; Objective: 50× and 150×; Optical Zoom: 1.0×; Tiling: 2×2. A KeyenceVK-X200 was used with the same setting for samples S19-S21.Two height profiles were obtained for each sample. Whenever possible, fields of view were chosen to give a good sampling of the topography. Slope analyses were applied to the surface height profiles. MATLAB software (MathWorks, Natick, Mass.) was used to calculate the slope distribution.

Average x-slope and y-slope were evaluated in a 1.65 micron interval about each pixel. Gradient magnitude was determined from x and y slope data, and evaluated in a 1.65 µm×1.65 µm box centered at each pixel. Gradient magnitude distribution, as well as x-slope and y-slope distribution were generated within a bin size of 0.5 degrees.

Results

Table 4 shows the Total CIE Chroma, as well as the minimum L* for scatter angle of 70° (Lmin70) and ratio of the minimum L* for scatter angle of 70° to maximum L* for Scatter Angle of 15° (Lmin70/Lmax15), each at incidence angle of 0°, for samples S1-S21.

TABLE 4

| Sample | Lmin70 | Lmin70/Lmax15 (L Ratio) | Total CIE Chroma |
|---|---|---|---|
| S1 | 27.55 | 0.169 | 4.173 |
| S2 | 53.17 | 0.425 | 2.077 |
| S3 | 46.93 | 0.466 | 6.762 |
| S4 | 53.12 | 0.444 | 2.675 |
| S5 | 44.80 | 0.280 | 2.175 |
| S6 | 41.54 | 0.230 | 3.81 |
| S7 | 29.54 | 0.137 | 2.403 |
| S8 | 74.86 | 0.793 | 4.504 |
| S9 | 76.43 | 0.893 | 7.825 |
| S10 | 52.36 | 0.245 | 2.869 |
| S11 | 66.07 | 0.524 | 0.959 |
| S12 | 53.16 | 0.254 | 2.22 |
| S13 | 65.96 | 0.518 | 0.952 |
| S14 | 28.55 | 0.128 | 5.408 |
| S15 | 71.89 | 0.702 | 2.816 |
| S16 | 53.22 | 0.356 | 0.716 |
| S17 | — | — | 4.151 |
| S18 | 57.84 | 0.818 | 0.084 |
| S19 | 57.76 | 0.442 | 1.841 |
| S20 | 55.40 | 0.422 | 2.042 |
| S21 | 55.47 | 0.375 | 1.741 |

Table 5 shows the Root Mean Squared Surface Roughnesses ($R_q$), minimum between the full width at half maximum (FWHM) for the x-slope distribution and the y-slope distribution, and mode and mean gradient magnitudes of slope ($\Delta x = 1.5$ wavelength) for Samples S1-S17, and S19-S21.

TABLE 5

| Sample | $R_q$ (µm) | Minimum of (xslope FWHM, yslope FWHM). | Gradient Magnitude of Slope, Mode (degrees) | Gradient Magnitude of Slope, Mean (degrees) |
|---|---|---|---|---|
| S1 | 0.48 | 4.90 | 2.250 | 8.470 |
| S2 | 1.68 | 21.38 | 9.750 | 19.574 |
| S3 | 1.10 | 28.11 | 14.750 | 25.924 |
| S4 | 1.26 | 26.06 | 10.250 | 24.105 |
| S5 | 1.17 | 17.99 | 6.750 | 18.082 |
| S6 | 0.94 | 2.77 | 1.500 | 12.491 |
| S7 | 0.65 | 1.78 | 1.250 | 7.438 |
| S8 | 1.98 | 35.75 | 17.000 | 25.946 |

TABLE 5-continued

| Sample | $R_q$ (μm) | Minimum of (xslope FWHM, yslope FWHM). | Gradient Magnitude of Slope, Mode (degrees) | Gradient Magnitude of Slope, Mean (degrees) |
|---|---|---|---|---|
| S9 | 2.06 | 44.83 | 21.500 | 25.690 |
| S10 | 1.30 | 13.79 | 6.500 | 18.870 |
| S11 | 1.67 | 23.65 | 10.750 | 21.844 |
| S12 | 1.32 | 15.68 | 6.750 | 18.913 |
| S13 | 1.61 | 24.88 | 10.750 | 21.656 |
| S14 | 0.26 | 4.59 | 2.500 | 4.388 |
| S15 | 1.98 | 33.53 | 14.500 | 19.246 |
| S16 | 0.49 | 12.44 | 7.250 | 11.133 |
| S17 | 0.20 | 1.79 | 1.250 | 2.730 |
| S18 | — | — | — | — |
| S19 | 0.55 | 15.03 | 7.00 | 9.23 |
| S20 | 0.28 | 14.15 | 6.00 | 7.59 |
| S21 | 0.28 | 11.42 | 4.75 | 7.31 |

Table 6 shows gloss measurements for Samples S1-S9 & S12-S18.

TABLE 6

| Sample | Gloss Units |
|---|---|
| S1 | 128.4 |
| S2 | 17.3 |
| S3 | 5.4 |
| S4 | 8.8 |
| S5 | 24.9 |
| S6 | 79.3 |
| S7 | 198.3 |
| S8 | 6.1 |
| S9 | 4.1 |
| S12 | 28.2 |
| S13 | 16.9 |
| S14 | 265.3 |
| S15 | 9.0 |
| S16 | 32.2 |
| S17 | 483.4 |
| S18 | 12.1 |

Laser Patterned Orthodontic Archwires

Laser patterned 304SS and NiTi orthodontic archwire prototypes were prepared as follows. Similar lengths of straight rectangular wires (304SS or NiTi, 0.46 mm×0.64 mm×~180-250 mm) were ganged together and attached to a flat substrate, such that the sidewalls of adjacent wires were in contact. The rectangular wires were oriented such that each surface to be patterned for each wire was at the same height relative to the focal spot position of the laser beam (stated another way, the collective surface of the ganged rectangular wires to be patterned was substantially flat). A ~10 mm×10 mm portion of the surface the ganged wired assembly was laser patterned with 2 passes, at 30 μm pitch, and 3.25 W (rotating the pattern by 90° between passes), in a similar fashion as previously described. The ganged wire assembly was then moved (translated) and the laser patterning repeated over an adjacent unpatterned region, such that adjacent ~10 mm—10 mm patterns overlapped by ~40 μm. Additional surfaces of the rectangular archwires were patterned simply by removing the wires from the flat substrate, rotating the wires by 90° to expose a new surface, reganging the wires, reattaching the ganged wires to the flat substrate, and repeating the patterning. Patterned, rectangular 304SS wires were hand-shaped to a suitable arch form for an orthodontic archwire. Patterned, rectangular NiTi wires may be shape set to an arch form at elevated temperatures, using conventional methods. Lastly, fully 360° patterned, NiTi round wires (0.46 mm) were prepared in a similar fashion as described for NiTi rectangular wires, except that the wires were rotated by ~120° to expose a new, unpatterned surface (and repeating the patterning).

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An orthodontic archwire comprising:
    an exterior surface including metal; and
    a plurality of engineered features on the exterior surface, wherein the engineered features include a plurality of recesses in the exterior surface, wherein the average depth of the plurality of recesses is at least 0.5 microns and no greater than 20 microns, wherein the pitch between adjacent recesses is at least 15 microns and no greater than 60 microns, and wherein the surface including the plurality of features provides an engineered surface that exhibits a Total CIE Chroma of no greater than 14 and a minimum L* value of at least 20 at an incident angle of 0 degrees and a view angle of 70 degrees, as measured by the Diffuse Scattering Test.

2. The orthodontic archwire of claim 1, wherein the recesses are arranged in an array having a transverse axis and a longitudinal axis, and wherein the pitch between adjacent recesses along the transverse axis is greater than a pitch between adjacent recesses along the longitudinal axis.

3. The orthodontic archwire of claim 2, wherein the cross-sectional dimension includes a diameter, the diameter is at least 25 and no greater than 35 microns, and wherein the pitch is at least 25 and no greater than 35 microns.

4. The orthodontic archwire of claim 1, wherein the plurality of recesses are arranged in a periodic array, and wherein the surface includes interstitial space between any two recesses in an array, and, wherein the interstitial space between recesses include one or more protrusive features.

5. The orthodontic archwire of claim 1 wherein at least one recess includes protrusive features on a bottom surface of the recess.

6. The orthodontic archwire of claim 1, wherein the surface exhibits a L* ratio of at least 0.4 in the absence of any aesthetic coating.

7. The archwire of claim 1 wherein at least one recess includes a depth of about 10 microns.

8. The orthodontic archwire of claim 1, the exterior surface is an electroplated metal coating.

9. The orthodontic archwire of claim 1, wherein an electroplated metal coating is disposed on the engineered surface.

10. The orthodontic archwire of claim 1, wherein at least 75% of the area of the engineered surface is contained within the recesses.

11. The orthodontic archwire of claim 8, wherein the electroplated metal coating comprises at least one of aluminum and rhodium.

12. The orthodontic archwire of claim 9, wherein at least one recess of the plurality of recesses is arranged in a unit cell with at least two other recesses, and wherein the pitch between recesses in the unit cell is at least 20 microns and no greater than 50 microns.

13. The orthodontic archwire of claim 9, wherein the electroplated metal coating comprises at least one of aluminum and rhodium.

* * * * *

UNITED STATES PATENT AND TRADEMARK OFFICE
CERTIFICATE OF CORRECTION

PATENT NO. : 10,543,061 B2  
APPLICATION NO. : 15/513365  
DATED : January 28, 2020  
INVENTOR(S) : Dan Skamser et al.

Page 1 of 1

It is certified that error appears in the above-identified patent and that said Letters Patent is hereby corrected as shown below:

In the Specification

Column 1, Line 67, delete "(Addle et al.)" and insert -- (Adelle et al.) --

Column 10, Line 11, delete "Where," and insert -- where, --

Column 14, Line 49, delete "(0" and insert -- ($_{di}$) --

Column 17, Line 20, delete "WO 2004/000569" and insert -- WO2004/000569 --

Column 17, Line 36, delete "WO 2009/045036" and insert -- WO2009/045036 --

Column 18, Line 50, delete "disclosure," and insert -- "disclosure. --

Column 21, Line 47, delete "embodiments" and insert -- embodiment --

Column 24, Line 20, delete "(~0.33-0.39 mm—~12.7 mm—~50.8 mm)" and insert -- (~0.33-0.39 mm × ~12.7 mm × ~50.8 mm) --

Column 29, Line 57, delete "~10 mm—10 mm" and insert -- ~ 10 mm X 10 --

In the Claims

Column 30, Line 47, insert -- , -- after "1"

Signed and Sealed this  
Thirty-first Day of August, 2021

Drew Hirshfeld  
*Performing the Functions and Duties of the*  
*Under Secretary of Commerce for Intellectual Property and*  
*Director of the United States Patent and Trademark Office*